US010779972B2

(12) United States Patent
Tunev et al.

(10) Patent No.: US 10,779,972 B2
(45) Date of Patent: Sep. 22, 2020

(54) DRUG-FILLED STENTS TO PREVENT VESSEL MICRO-INJURIES AND METHODS OF MANUFACTURE THEREOF

(71) Applicant: Medtronic Vascular, Inc., Santa Rosa, CA (US)

(72) Inventors: Stefan Tunev, Santa Rosa, CA (US); Ryan Bienvenu, Santa Rosa, CA (US); Justin Peterson, Santa Rosa, CA (US); Carol Sullivan, Santa Rosa, CA (US); Christopher Storment, Santa Rosa, CA (US); Michael Harms, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 80 days.

(21) Appl. No.: 15/808,598

(22) Filed: Nov. 9, 2017

(65) Prior Publication Data

US 2018/0125685 A1    May 10, 2018

Related U.S. Application Data

(60) Provisional application No. 62/420,473, filed on Nov. 10, 2016, provisional application No. 62/420,484, filed on Nov. 10, 2016.

(51) Int. Cl.
*A61F 2/86* (2013.01)
*A61F 2/88* (2006.01)
(Continued)

(52) U.S. Cl.
CPC ............... *A61F 2/88* (2013.01); *A61F 2/856* (2013.01); *A61F 2/86* (2013.01); *A61F 2/89* (2013.01);
(Continued)

(58) Field of Classification Search
CPC ........ A61F 2/82–945; A61F 2250/0025–0026; A61F 2250/0051–0052; A61F 2250/0067–0068; A61F 2/86–88
See application file for complete search history.

(56) References Cited

U.S. PATENT DOCUMENTS 4,800,882 A    1/1989   Gianturco
4,886,062 A   12/1989   Wiktor
(Continued)

FOREIGN PATENT DOCUMENTS

WO    2008/063780 A2    5/2008
WO    2008/106223 A1    9/2008
WO    2014/162902 A1   10/2014

OTHER PUBLICATIONS

Cwikiel W et al, "Electrolytic Stents to Inhibit Tumor Growth. An experimental study in vitro and in rats," Acta Radiologica, Informa Healthcare, GB, vol. 34, No. 3, May 1, 1993 (May 1, 1993), pp. 258-262.

(Continued)

*Primary Examiner* — Rebecca S Preston
(74) *Attorney, Agent, or Firm* — Medler Ferro Woodhouse & Mills PLLC

(57) ABSTRACT

A stent includes a hollow wire formed into a stent pattern. The hollow wire includes an outer member, a lumen extending longitudinally within the hollow wire, at least one opening extending from an outer surface of the outer member to the lumen, and a surface area component within the hollow wire. The surface area component increases the amount of surface area available for tissue in-growth within the hollow wire. More than one surface area component may be utilized. Each surface area component may be disposed within the lumen or the at least one opening of the hollow (Continued)

wire. A pharmacologically or biologically active agent may be disposed within the lumen.

18 Claims, 15 Drawing Sheets

(51) Int. Cl.
  *A61F 2/856* (2013.01)
  *A61F 2/89* (2013.01)
  *A61F 2/91* (2013.01)
  *A61F 2/915* (2013.01)
  *A61F 2/848* (2013.01)
  *A61F 2/00* (2006.01)

(52) U.S. Cl.
  CPC ............... *A61F 2/91* (2013.01); *A61F 2/848* (2013.01); *A61F 2002/0086* (2013.01); *A61F 2002/91541* (2013.01); *A61F 2210/0076* (2013.01); *A61F 2220/005* (2013.01); *A61F 2230/0006* (2013.01); *A61F 2230/0013* (2013.01); *A61F 2230/0069* (2013.01); *A61F 2240/001* (2013.01); *A61F 2250/0015* (2013.01); *A61F 2250/0021* (2013.01); *A61F 2250/0025* (2013.01); *A61F 2250/0026* (2013.01); *A61F 2250/0032* (2013.01); *A61F 2250/0039* (2013.01); *A61F 2250/0051* (2013.01); *A61F 2250/0067* (2013.01); *A61F 2250/0068* (2013.01); *A61F 2250/0098* (2013.01)

(56) References Cited

U.S. PATENT DOCUMENTS

| | | | |
|---|---|---|---|
| 5,019,090 A | 5/1991 | Pinchuk | |
| 5,133,732 A | 7/1992 | Wiktor | |
| 5,599,291 A * | 2/1997 | Balbierz | A61L 27/34 |
| | | | 604/264 |
| 5,782,903 A | 7/1998 | Wiktor | |
| 6,136,023 A | 10/2000 | Boyle | |
| 6,805,898 B1 * | 10/2004 | Wu | A61F 2/0077 |
| | | | 216/10 |
| 6,908,447 B2 * | 6/2005 | McWeeney | A61F 2/0022 |
| | | | 604/9 |
| 7,167,746 B2 | 1/2007 | Pederson | |
| 7,682,388 B2 | 3/2010 | Rea | |
| 2005/0033265 A1 * | 2/2005 | Engel | A61B 17/3421 |
| | | | 604/523 |
| 2007/0043423 A1 * | 2/2007 | Grewe | A61F 2/885 |
| | | | 623/1.11 |
| 2007/0244536 A1 | 10/2007 | Pederson | |
| 2007/0270942 A1 | 11/2007 | Thomas | |
| 2008/0249457 A1 * | 10/2008 | Li | A61M 25/0041 |
| | | | 604/8 |
| 2009/0023004 A1 | 1/2009 | Pederson | |
| 2009/0187254 A1 | 7/2009 | Deal et al. | |
| 2010/0303882 A1 | 12/2010 | Cantrell et al. | |
| 2011/0245904 A1 | 10/2011 | Pacetti et al. | |
| 2011/0251668 A1 | 10/2011 | Thompson et al. | |
| 2012/0067103 A1 * | 3/2012 | Bienvenu | A61F 2/88 |
| | | | 72/369 |
| 2013/0274864 A1 | 10/2013 | Bienvenu et al. | |
| 2015/0297803 A1 | 10/2015 | Pulugurtha | |
| 2017/0354521 A1 * | 12/2017 | Ryan | A61F 2/89 |

OTHER PUBLICATIONS

International Search Report and the Written Opinion of the International Searching Authority issued in PCT/US2017/060958, dated Jan. 31, 2018.

Lee, Jung-Jin et al., "Evaluation of Effect of Galvanic Corrosion Between Nickel-Chromium Metal and Titanium on Ion Release and Cell Toxicity" J Adv Prosthodont 2015;7:172-7, pp. 1-6.

Devine, D.M. et al., "Tissue Reaction to Implants of Different Metals: A Study Using Guide Wires in Cannulated Screws" www.ecmjournal.org, European Cells and Materials, vol. 18 2009 (pp. 40-48), pp. 40-48.

Sansone, Valerio et al., "The Effects on Bone Cells of Metal Ions Released From Orthopaedic Implants. A Review" Clinical Cases in Mineral and Bone Metabolism 2013; 10(1): 34-40.

Acevedo, Daniel, MD et al., "Mixing Implants of Differing Metallic Composition in the Treatment of Upper-Extremity Fractures" www.healio.com/orthopedics/journals/ortho, Orthopedics, Sep. 2013, vol. 36, Issue 9, e1175-e1179.

* cited by examiner

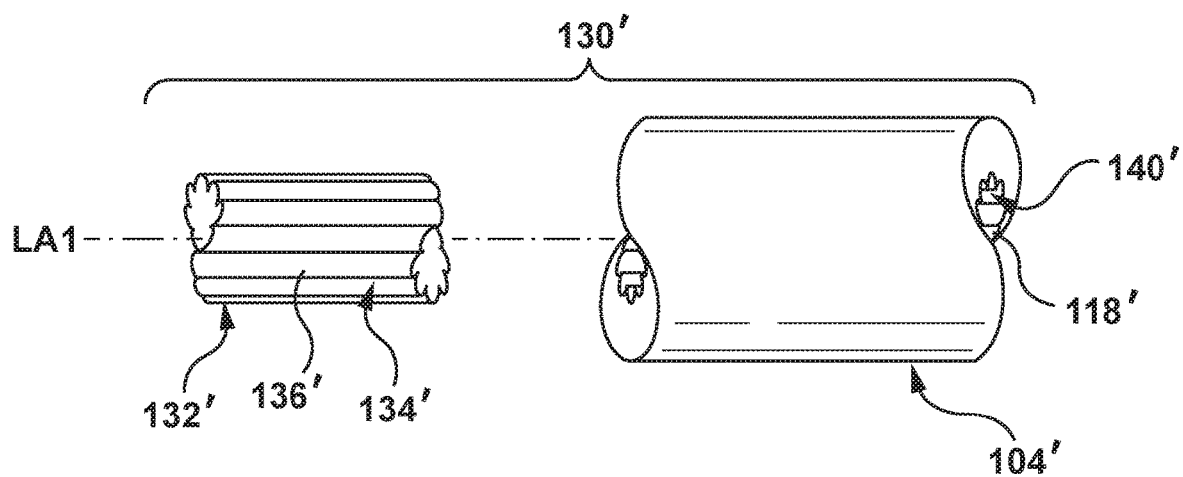
FIG. 9
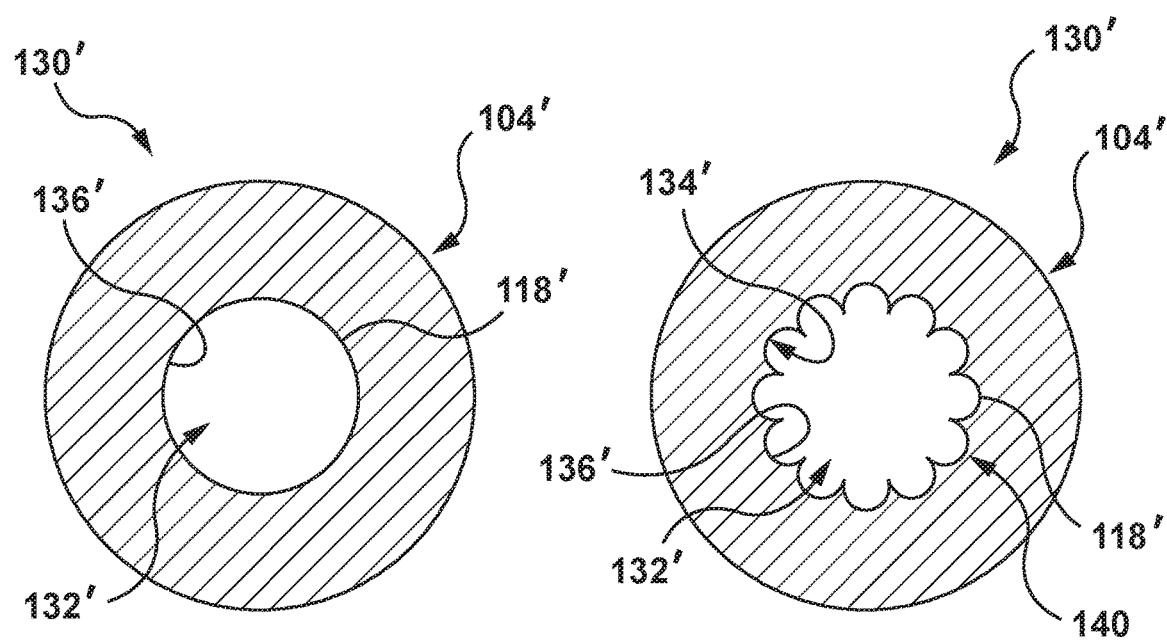
FIG. 10
FIG. 11

DRUG-FILLED STENTS TO PREVENT VESSEL MICRO-INJURIES AND METHODS OF MANUFACTURE THEREOF

CROSS REFERENCE TO RELATED APPLICATIONS

This application claims the benefit under 35 U.S.C. § 119(e) of the filing date of U.S. Provisional Application No. 62/420,473, filed Nov. 10, 2016, and U.S. Provisional Application No. 62/420,484, filed Nov. 10, 2016, the contents of each of which are incorporated by reference herein, in their entirety.

FIELD OF THE INVENTION

The present invention relates to drug-filled stents and methods of manufacturing drug-filled stents. More particularly, the present invention relates to drug-filled stents with an increased surface area to promote tissue in-growth and methods of manufacture thereof.

BACKGROUND OF THE INVENTION

Drug-eluting implantable medical devices, such as stents, have become popular for their ability to perform their primary function (such as structural support) and their ability to medically treat the area in which they are implanted.

For example, drug-eluting stents have been used to prevent restenosis in coronary arteries. Drug-eluting stents may administer therapeutic agents (hereafter referred to as "drugs") such as anti-inflammatory compounds that block local invasion/activation of monocytes, thus preventing the secretion of growth factors that may trigger vascular smooth muscle cell (VSMC) proliferation and migration. Other potentially anti-restenotic compounds include antiproliferative agents, such as chemotherapeutics, which include rapamycin and paclitaxel. Other classes of drugs such as anti-thrombotics, anti-oxidants, platelet aggregation inhibitors and cytostatic agents have also been suggested for anti-restenotic use.

Drug-eluting medical devices may be coated with a polymeric material which, in turn, is impregnated with a therapeutic agent or a combination of therapeutic agents. Once the medical device is implanted at a target location, the therapeutic agent(s) is released from the polymer for treatment of the local tissues. The therapeutic agent(s) is released by a process of diffusion through the polymer layer for biostable polymers, and/or as the polymer material degrades for biodegradable polymers.

Controlling the rate of elution of a drug from the drug impregnated polymeric material is generally based on the properties of the polymer material. However, at the conclusion of the elution process, the remaining polymer material in some instances has been linked to an adverse reaction with the vessel, possibly causing inflammation or a small but dangerous clot to form. Further, drug impregnated polymer coatings on exposed surfaces of medical devices may flake off or otherwise be damaged during delivery, thereby preventing the drug from reaching the target site. Still further, drug impregnated polymer coatings are limited in the quantity of the drug to be delivered by the amount of a drug that the polymer coating can carry and the size of the medical devices. Controlling the rate of elution using polymer coatings is also difficult.

Stents with hollow, drug-filled structural members have been contemplated and developed. For example, U.S. Pat. No. 6,071,305 to Brown et al., generally discloses a stent formed of an elongated member in a spiral tube configuration. The elongated member includes a groove that can be filled with an active agent. Further, U.S. Pat. No. 9,283,305 to Birdsall et al., U.S. Application Publication No. 4011/0070358 to Mauch et al., U.S. Pat. No. 8,460,745 to Mitchell et al., and U.S. Pat. No. 9,119,739 to Thompson, each of which is herein incorporated by reference in its entirety, describe methods of forming and filling stents with hollow, drug-filled structural members from composite wires. There remains a need in the art for improvements of drug-filled stents.

BRIEF SUMMARY OF THE INVENTION

Embodiments hereof relate to a stent including a hollow wire formed into a stent pattern. The hollow wire includes an outer member, a lumen, at least one opening, and at least one surface area component. The lumen extends longitudinally within the hollow wire. The at least one opening extends through the outer member to the lumen and is defined by a radial surface. The at least one surface area component is disposed within the hollow wire and increases the amount of surface available for tissue in-growth within the hollow wire.

Embodiments hereof further relate to a stent including a hollow wire formed into a stent pattern. The hollow wire includes an outer member, a lumen, at least one opening, and a surface area component. The outer member includes an outer surface. The lumen is defined by an inner surface of the hollow wire and extends longitudinally within the hollow wire. The at least one opening is defined by a radial surface and is disposed through the outer member to the lumen. The surface area component is disposed on at least one radial surface of the at least one opening or on the inner surface of the hollow wire defining the lumen. A first diameter of the at least one opening at the outer surface of the outer member is greater than a second diameter of the lumen. The surface area component increases the amount of surface available for tissue in-growth within the hollow wire.

Embodiments hereof further relate to a method of forming a stent. A composite wire is processed to form a surface area component. The composite wire includes an outer member and a core member and the surface area component is a roughness on an inner surface of the outer member. The composite wire is shaped into a stent pattern. Openings are provided through the outer member to the core member. The composite wire is processed to remove the core member without adversely affecting the outer member or the at least one surface area component.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 9 is a schematic illustration of a composite wire which may be utilized for forming a stent in the method of FIG. 4 in accordance with another embodiment hereof, the composite wire including an outer member, a core member, and a surface area component.

FIG. 10 is a cross-sectional view of the composite wire of FIG. 9 at a step in the method of FIG. 4, wherein the plurality of openings has not been provided, the core member has not been processed for removal, and the outer member and the core member have not been processed to form the surface area component.

FIG. 11 is a cross-sectional view of the composite wire of FIG. 9 at a step in the method of FIG. 4, wherein the plurality of openings has not been provided and the core member has not been processed for removal, but the outer member and the core member have been processed to form the surface area component.

DETAILED DESCRIPTION OF THE INVENTION

Specific embodiments of the present invention are now described with reference to the figures, wherein like reference numbers indicate identical or functionally similar elements.

The following detailed description is merely exemplary in nature and is not intended to limit the invention or the application and uses of the invention. Although the description of embodiments hereof is in the context of drug-filled medical devices for delivering therapeutic agents within a body vessel, medical devices described herein can also be used in other parts of the body. Furthermore, there is no intention to be bound by any expressed or implied theory presented in the preceding technical field, background, brief summary or the following detailed description.

Figure 1:
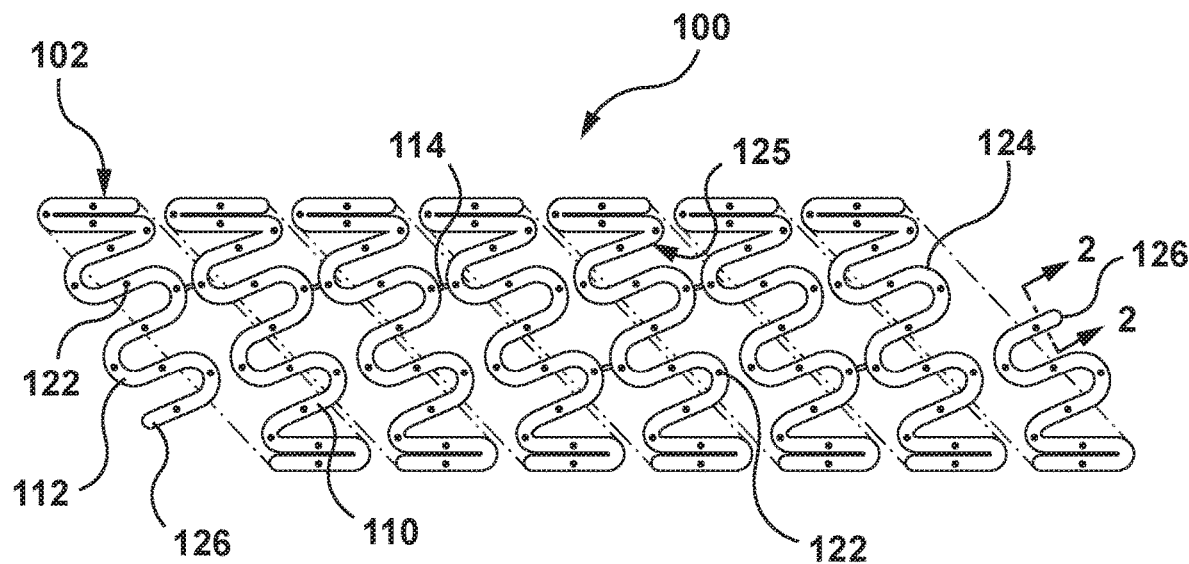
FIG. 1 is a schematic illustration of a stent in accordance with an embodiment hereof, wherein the stent is formed from a hollow wire with a surface area component and an active agent disposed within the lumen of the hollow wire, wherein the surface area component is a roughness forming an increased amount of surface within the lumen of the hollow wire.
Figure 2:
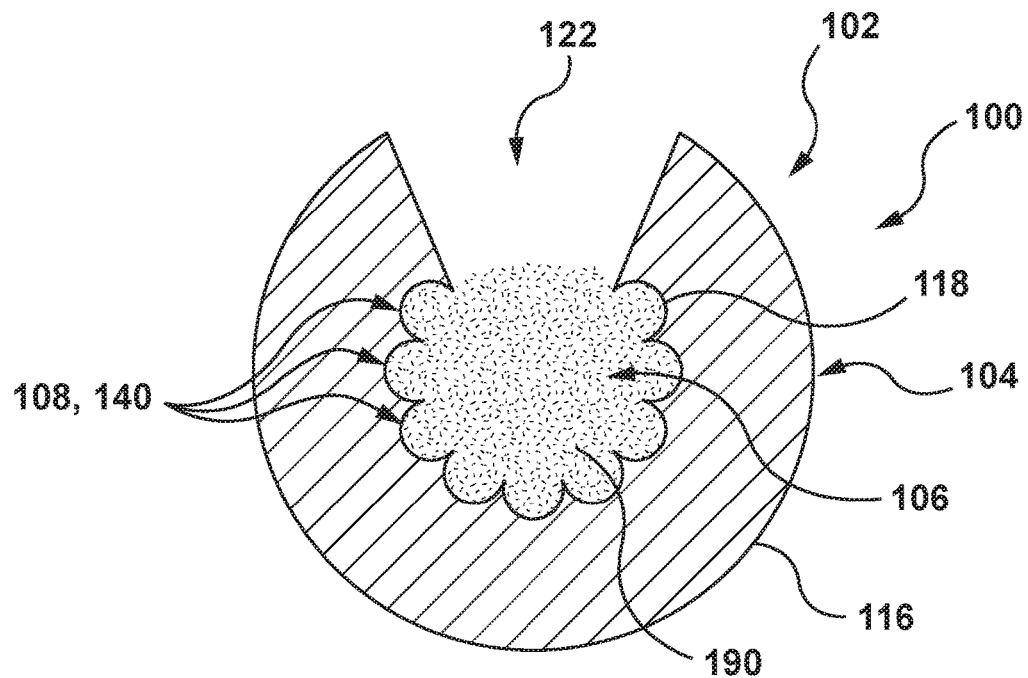
FIG. 2 is a cross-sectional view taken along line 2-2 of FIG. 1.

A stent 100 in accordance with an embodiment hereof is described herein and shown in FIGS. 1 and 2. The stent 100 is formed from a hollow wire 102. The hollow wire 102 includes an outer member 104, a lumen 106 defined by an inner surface 118 of the outer member 104 and extending longitudinally within the outer member 104. The hollow wire further includes a plurality of openings 122 extending through the outer member 104 to the lumen 106, and a surface area component 108 disposed or formed on the inner surface 118 of the outer member. In the embodiment of FIGS. 1 and 2, the surface area component 108 is a first roughness 140 integrally formed on the inner surface 118 of the outer member 104. The term "wire" as used herein means an elongated element or filament or group of elongated elements or filaments and is not limited to a particular cross-sectional shape or material, unless so specified.

In the embodiment of FIG. 1, the hollow wire 102 is formed into a series of generally sinusoidal waveforms including generally straight segments or struts 110 joined by bent segments or crowns 112. The waveform is helically wound to form the stent 100 into a generally tubular configuration. In the embodiment shown in FIG. 1, selected crowns 112 of longitudinally adjacent sinusoids may be joined by, for example, fusion points 114. However, the invention is not limited to the pattern or configuration shown in FIG. 1. The hollow wire 102 of the stent 100 can be formed into any pattern suitable for use as a stent. For example, and not by way of limitation, the hollow wire 102 of the stent 100 can be formed into patterns disclosed in U.S. Pat. No. 4,800,882 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is herein incorporated by reference in its entirety. Further, instead of a single length of hollow wire formed into a stent pattern, a plurality of hollow wires may be formed into a waveform and wrapped into individual annular elements. The annular elements may then be aligned along a common longitudinal axis and joined together to form a stent having a generally tubular configuration.

As described above and best shown in FIG. 2, the hollow wire 102 includes the outer member 104. In the embodiment of FIG. 2, the lumen 106 is defined or formed from the hollow portion of the outer member 104. In this embodiment, the surface area component 108 is the first roughness 140, which is formed on the inner surface 118 of the outer member 104 within the lumen 106 and extends longitudinally for the full or entire length of the hollow wire 102. The surface area component 108 is configured to increase the amount of surface, or surface area, within the hollow wire 102, and more specifically within the lumen 106, for improved tissue in-growth as described in more detail below. While the first roughness 140 is shown with a specific pattern, this is by way of example and not limitation, and the first roughness 140 may assume other shapes, and/or patterns. Additionally, while the hollow wire 102 is shown as generally having a circular cross-section, the hollow wire 102 may have other cross-sectional shapes such as, but not limited to a generally elliptical or rectangular cross-section. In some embodiments, the cross-sectional shape and/or size can vary along one or more segments of the hollow wire 102.

Although the surface area component 108 has been described herein as extending the entire or full length of the hollow wire 102, this is by way of example and not limitation. It will be understood that the surface area component 108 may extend a distance or length less than the entire or full length of the hollow wire 102. Additionally, the surface area component 108 may be discontinuous and start and stop along the length of the hollow wire 102 to form segments of the surface area component 108 along the length of the hollow wire 102. Further, the segments of the surface area component 108 may be positioned at select portions or locations of the stent 100 such as one or more crowns 112, one or more struts 110, or any combination thereof. In another embodiment, the segments of the surface area component 108 may be positioned at the end portions of the stent 100. Positioning of the segments of the surface area component 108 at select locations of the stent 100 may be utilized to encourage preferred tissue in-growth in select locations.

Figure 3A:
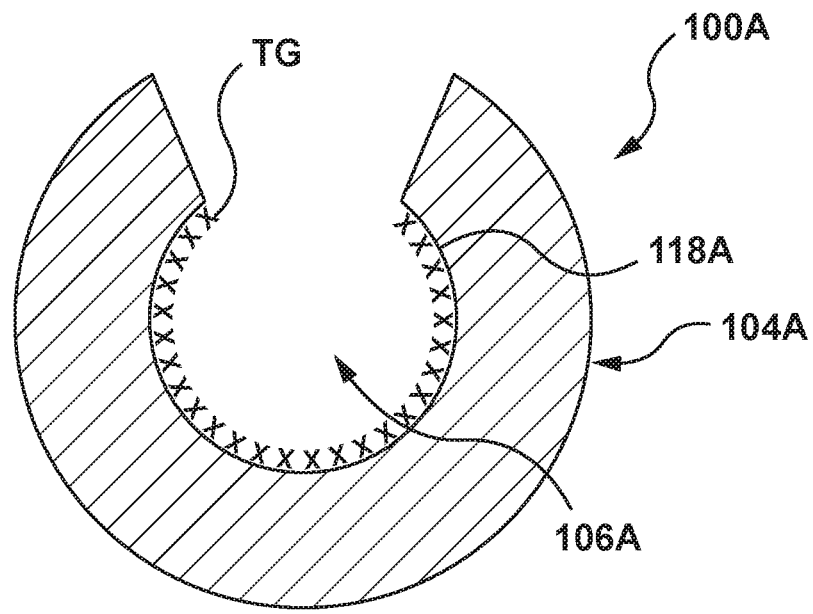
FIG. 3A is also a cross-sectional view of the hollow wire of FIG. 1, wherein the surface area component and the active agent have been omitted to illustrate a surface area within a lumen without the surface area component.
Figure 3B:
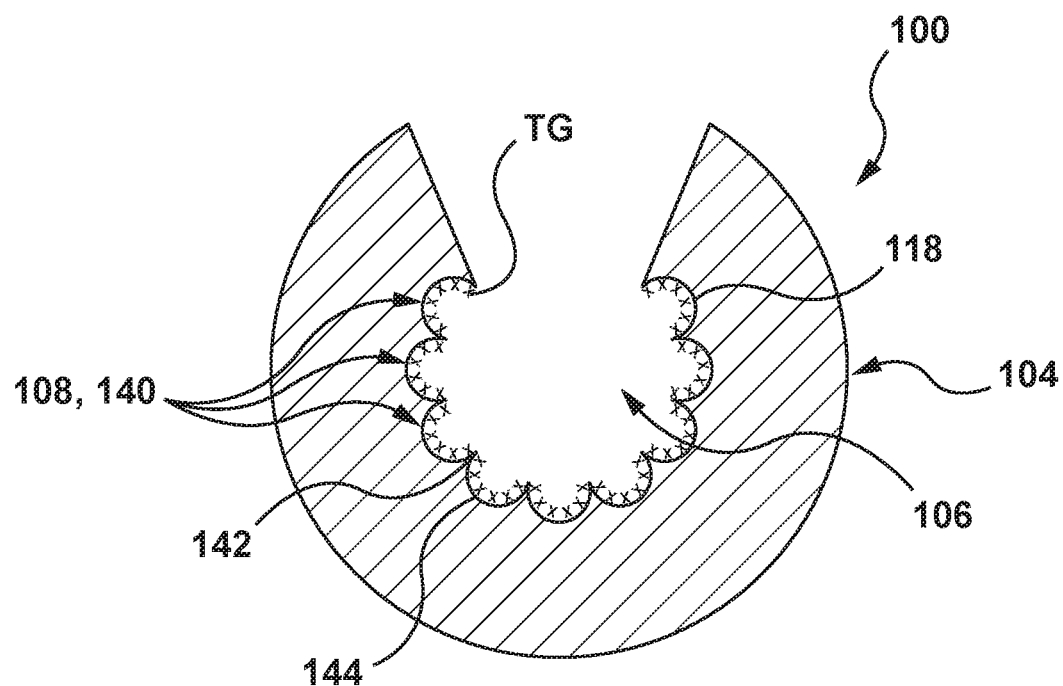
FIG. 3B is a cross-sectional view of the hollow wire of FIG. 1, wherein surface area component is shown to illustrate the increased amount of surface within the lumen with the surface area component and to illustrate the tissue growth about the surface area component after the active agent has eluted in situ.

FIGS. 3A and 3B illustrate the stent 100 without and with the surface area component 108, which in this embodiment is the first roughness 140, and are included herein to illustrate the increase in the amount of surface within the lumen 106 due to the inclusion of the surface area component 108. Referring to FIG. 3A, when the surface area component 108 is not included, the surface area available for tissue in-growth within the lumen 106A is only the smooth inner surface 118A of the outer member 104A. Stated another way, tissue TG may attach to the stent 100A within the lumen 106A only along the smooth inner surface 118A of the outer member 104A. However, as shown in FIG. 3B, when the surface area component 108, i.e., the first roughness 140, is included on the inner surface 118 of the outer member 104, the surface area available for tissue in-growth within the lumen 106 includes the roughened inner surface 118 of the outer member 104, including a plurality of peaks 142 and a plurality of valleys 144 formed in the inner surface 118 of the outer member 104. Due to the plurality of peaks 142 and the plurality of valleys 144, the roughened inner surface 118 has a greater amount of surface or surface area than the smooth inner surface 118A. Thus, the surface area component 108 increases the amount of surface available for tissue TG in-growth within the lumen 106 of the stent 100.

In the embodiment of FIG. 2, a biologically or pharmacologically active agent 190 (hereafter referred to as "active agent 190" for simplicity) is deposited within the lumen 106 of the hollow wire 102. In the embodiment of FIG. 2, the plurality of openings 122 provide access to the lumen 106 to permit the active agent 190 to be released from the lumen 106. Further, the plurality of openings 122 provide access to the lumen 106 to permit tissue in-growth into the lumen 106 after the active agent 190 has been released from the lumen 106. The plurality of openings 122 may be sized and shaped as desired to control both the elution rate of the active agent 190 from the lumen 106 and to control the in-growth of cells into the lumen 106 of the stent 100. Larger sized openings 122 generally permit a faster elution rate and a faster in-growth rate and smaller sized openings 122 generally provide a slower elution rate and a slower in-growth rate. The size and/or quantity of the plurality of openings 122 may be varied along the stent 100 in order to vary both the quantity and/or rate of the active agent 190 being eluted from stent 100 and the in-growth of cells into the lumen 106 at different portions of stent 100. The plurality of openings 122 may be, for example and not by way of limitation, 10-30 μm in diameter. While shown in FIG. 1 with the plurality of openings 122 on an outwardly facing or abluminal surface 124, the is by way of example and not limitation, and the plurality of openings 122 may be provided on the abluminal surface 124 and/or on an inward facing or luminal surface 125, or may be provided anywhere along the circumference of the hollow wire 102.

As used herein, a biologically or pharmacologically active agent may include, but is not limited to, antineoplastic, antimitotic, anti-inflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include ABT-578 (a synthetic analog of rapamycin), rapamycin (sirolimus), zotarolimus, everolimus, angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other active substances or agents that may be used include nitric oxide, alpha-interferon, genetically engineered epithelial cells, and dexamethasone. In other examples, the active substance is a radioactive isotope for implantable device usage in radioactive procedures. Examples of radioactive isotopes include, but are not limited to, phosphorus ($P^{32}$), palladium ($Pd^{103}$), cesium ($Cs^{131}$), Iridium ($I^{192}$) and iodine ($I^{125}$). While the preventative and treatment properties of the foregoing active substances or agents are well-known to those of ordinary skill in the art, the substances or agents are provided by way of example and are not meant to be limiting. Other active substances are equally applicable for use with the disclosed methods and compositions. Further, a carrier may be used with the biologically or pharmacologically active agent. Examples of suitable carriers include, but are not limited to, ethanol, acetone, tetrahydrofuran, dymethylsulfoxide, a combination thereof, or other suitable carriers known to those skilled in the art. Still further, a surfactant may be formulated with the drug and the solvent to aid elution of the drug.

The ends 126 of the hollow wire 102 may be closed by crimping excess material of the hollow wire 102 to close the lumen 106. The ends 126 may also be closed by not removing a core member during the method of manufacture thereof, described in more detail below, from the ends 126. In the embodiment of FIG. 2, with the active agent 190 disposed within the lumen 106, closing the ends 126 prevents the active agent 190 from prematurely releasing from the ends 126. However, closing the ends 126 is not required as the active agent 190 may be dried, provided within a polymer matrix, enclosed within a liner (not shown in FIGS. 1 and 2), or otherwise protected from premature release from the ends 126. Further, the ends 126 may be welded, crimped or otherwise connected to other portions of the hollow wire 102 such that the ends 126 are not free ends.

When the stent 100 is deployed within a vessel, the active agent 190 elutes from the lumen 106 of the stent 100. Once the active agent 190 has been eluted, cells originating from the vessel migrate through the plurality of openings 122 and into the lumen 106. The cells attach or couple to the surfaces within the lumen 106. More specifically, the cells couple to the inner surface 118 of the outer member 104, which includes the first roughness 140 as shown in FIG. 3B described above. Once attached thereto, the cells grow or colonize and form an extracellular matrix within the lumen 106 of the stent 100 to couple the stent 100 to the vessel. The increased amount of surface available within the lumen 106 of the hollow wire 102 due to the surface area component 108 permits more cells to couple to the stent 100, and thus more firmly anchors the stent 100 to the vessel. The improved mechanical integration, or coupling of the stent 100 to the vessel, may offer clinical benefit in reducing micro-damage to the tissue surrounding the stent 100 during biomechanical motion of the vessel, such as the repetitive constriction and dilation of the vessel due to cardiac pressure differentials of the cardiac cycle. The term "micro-damage," as used herein, means tissue damage due to the relative movement between a generally rigid stent and a generally flexible vessel. Further, the term "biomechanical motion," as used herein means the motion or movement of a vessel. For example, and not by way of limitation, biomechanical motion includes the repetitive constriction and dilation of a body vessel due to cardiac pressure differentials of the cardiac cycle.

Figure 4:
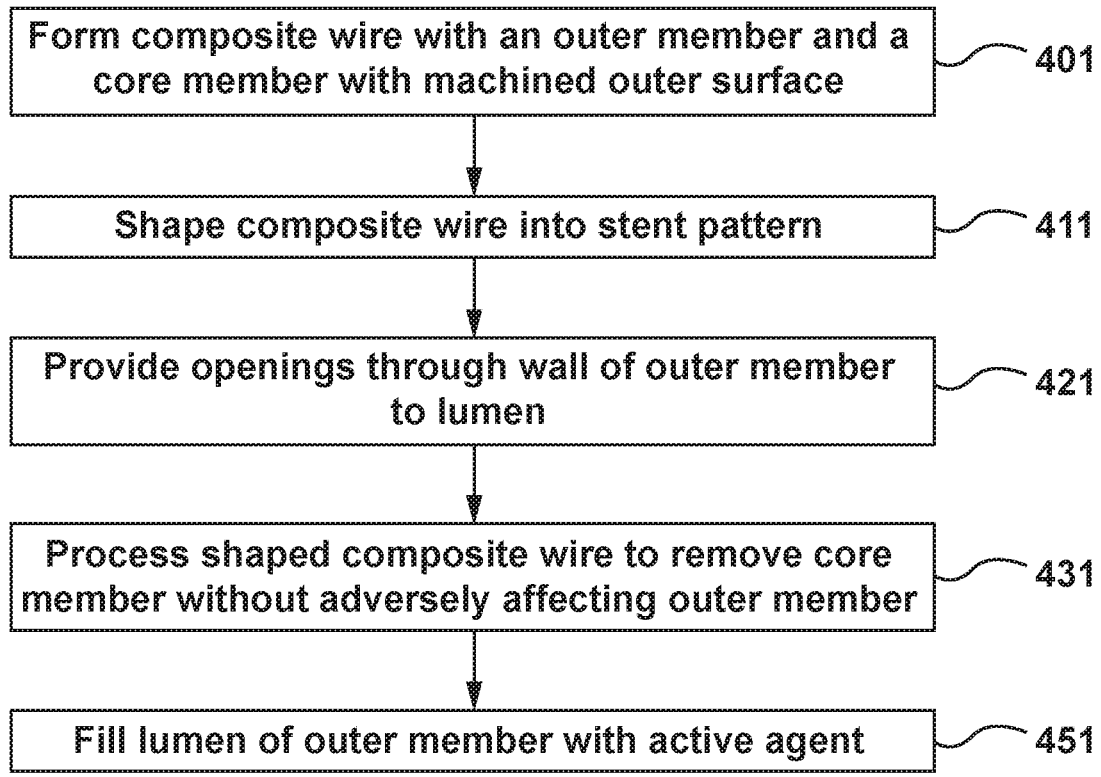
FIG. 4 is flow chart illustrating an embodiment of a method of forming the stent of FIG. 1.
Figure 5:
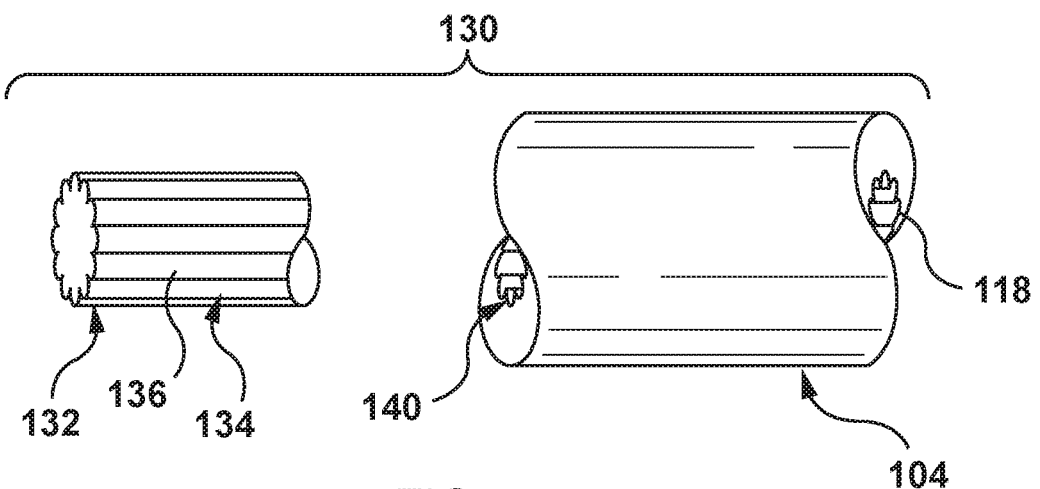
FIG. 5 is a schematic illustration of a composite wire which may be utilized for forming a stent in the method of FIG. 4, the composite wire including an outer member, a core member, and a surface area component.
Figure 6:
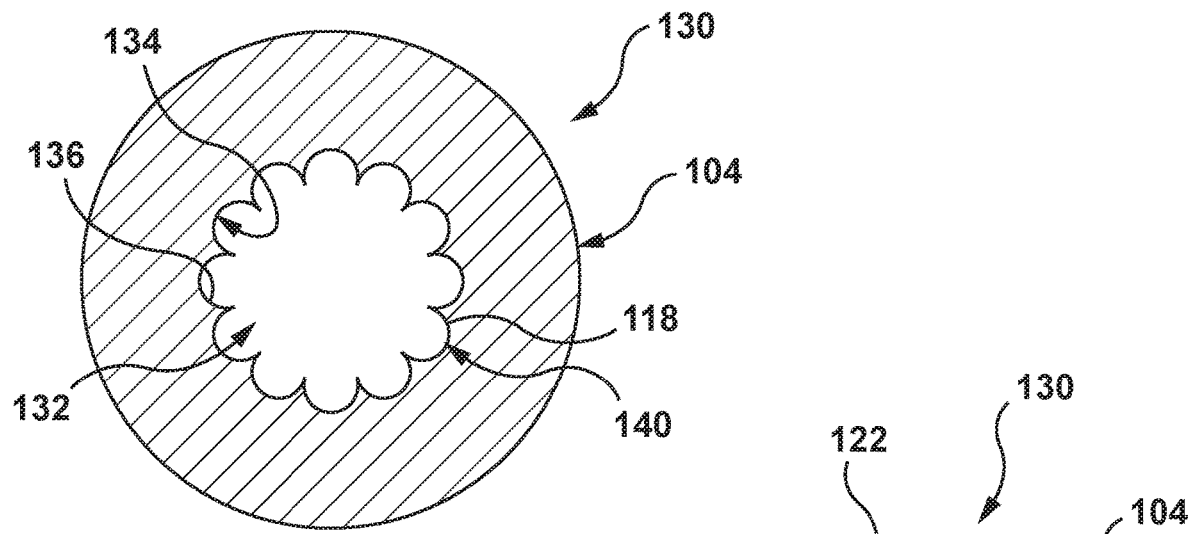
FIG. 6 is a cross-sectional view of the composite wire of FIG. 5 at a step in the method of FIG. 4, wherein the plurality of openings has not been provided and the core member has not been processed for removal.

FIGS. 4-7 show a method for forming a stent from a hollow wire, such as the stent 100, in accordance with an embodiment hereof. As shown in FIG. 4, step 401 is to utilize a composite wire 130 having the outer member 104 with the first roughness 140 on the inner surface 118 of the outer member 104, and a core member 132 with a second roughness 134 on an outer surface 136 of the core member 132, as shown schematically in FIG. 5 and in cross-section in FIG. 6. FIGS. 5 and 6 illustrate the composite wire 130 after processing thereof is complete, i.e., after the composite wire 130 is formed as will be described in more detail herein. After manufacture or forming of the composite wire 130 is complete, the first roughness 140 on the inner surface 118 of the outer member 104 corresponds or mates with the second roughness 134 on the outer surface 136 of the core member 132. The first roughness 140 on the inner surface 118 of the outer member 104 is formed via the second roughness 134 on the outer surface 136 of the core member 132, as will be explained in more detail herein. The outer member 104 forms the hollow wire 102 of the stent 100 described above with respect to FIGS. 1 and 2 after processing thereof to form the stent 100.

The outer member 104 may be any material that is suitable to be used as a stent. More particularly, the requirements for the material of the outer member 104 are that it be biocompatible, sufficiently resilient to be used as a stent, that it survives the process for eliminating the core member 132, and that it is softer than the core material 132, as described in more detail below. The term "softer" as used here in, means that the material or substance is more easily molded or compressed than a comparative material or substance. For example, and not by way of limitation, the outer member 122 may be a cobalt-chromium alloy. As used herein, the term "cobalt-chromium" alloy includes alloys with cobalt and chromium. Generally, materials such as, but not limited to, cobalt-nickel-chromium alloys ("MP35N" and "MP20N") and chromium-nickel-tungsten-cobalt alloys ("L605") and cobalt-chromium-nickel-molybdenum alloys ("ELGILOY") are the types of materials included in the term "cobalt-chromium alloys" as used herein.

The core member 132 is a sacrificial material that is removed without damaging the outer member 104 and is harder than the outer member 104. The term "harder" as used here in, means that the material or substance is more resistant to pressure than a comparative material or substance. Prior to assembly into composite wire 130, the outer surface 136 of the core member 132 includes the second roughness 134. The second roughness 134 may be formed on the outer surface 136 of the core member 132 by methods such as, but not limited to machining, etching, or any other suitable method. Prior to assembly into composite wire 130, the inner surface 118 of the outer member 104 is smooth and does not yet include the first roughness 140. To form or assemble the composite wire 102, the core member 132 is disposed within the outer member 104. The outer member 104 with the core member 132 disposed therein are processed to form the composite wire 130, as shown in FIG. 6. The composite wire 130 may be formed by any processing method known in the art, for example and not by way of limitation, a co-drawing process, extrusion, cladding, or any other suitable method. Stated another way, the composite wire 130 may be formed by methods of forming composite wires known to those skilled in the art. Examples of composite wires and methods of forming composite wires can be found in U.S. Pat. No. 5,630,840 to Mayer, U.S. Pat. No. 6,248,190 to Stinson, U.S. Pat. No. 6,497,709 to Heath, and U.S. Pat. No. 7,101,392 to Heath, each of which is herein incorporated by reference in its entirety. In a non-limiting example, the composite wire 130 is formed via a drawn filled tubing (DFT) process. During processing of the outer member 104 and the core member 132, the softer outer member 104 is radially compressed over the harder core member 132 such that the second roughness 134 on the outer surface 136 of the core member 132 is imprinted on, or forms the corresponding first roughness 140 onto the inner surface 118 of the outer member 104.

In a non-limiting example, the outer member 104 is made of MP35N and the core member 132 is made of molybdenum (Mo). In the example, the process to remove the core member 132 which is described in more detail herein includes exposing the core member 132 to xenon difluoride gas (XeF2). Other examples of material combinations of the outer member 104, the core member 132, and the removal method are provided herein in chart form.

Referring back to FIG. 4, step 411 is to shape the composite wire 130 into the stent pattern. As discussed above, the stent pattern can be the pattern shown in FIG. 1 or any other suitable pattern formed from a wire. Further, although the order of all the steps is not critical, step 411 should be performed prior to removing the core member 132, as explained below. The step of shaping the composite member 130 into the stent pattern does not have to include shaping the composite member 130 into the final stent pattern. For example, the step 411 of shaping the composite member 130 into a stent pattern may include only forming the struts 110 and the crowns 112 in the composite wire 130. Shaping the composite wire 130 into the stent pattern while the core member 132 is disposed within the outer member 104 helps prevent kinking or other deformations from occurring in the outer member 104. Shaping the composite wire 130 into the stent pattern shown in FIG. 1 generally includes the steps of forming the composite wire 130 into a waveform pattern followed by wrapping the pattern around a mandrel, as known to those skilled in the art. The end result is a helical stent pattern formed onto a mandrel. Selected crowns 112 of the helical pattern may then be fused together and the stent may be removed from the mandrel. Step 411 of shaping the composite wire 130 into the stent pattern can be performed with techniques known to those skilled in the art. For example, and not by way of limitation, forming the composite wire 130 into a two dimensional waveform can be achieved using techniques described in U.S. Application Publication No. 4010/0269950 to Hoff et al. and U.S. Pat. No. 9,296,034 to Costa et al., each of which is herein incorporated by reference in its entirety, and U.S. Application Publication No. 4011/0070358 to Mauch et al., previously incorporated by reference. Other techniques understood by persons skilled in the art could also be used.

Figure 7:
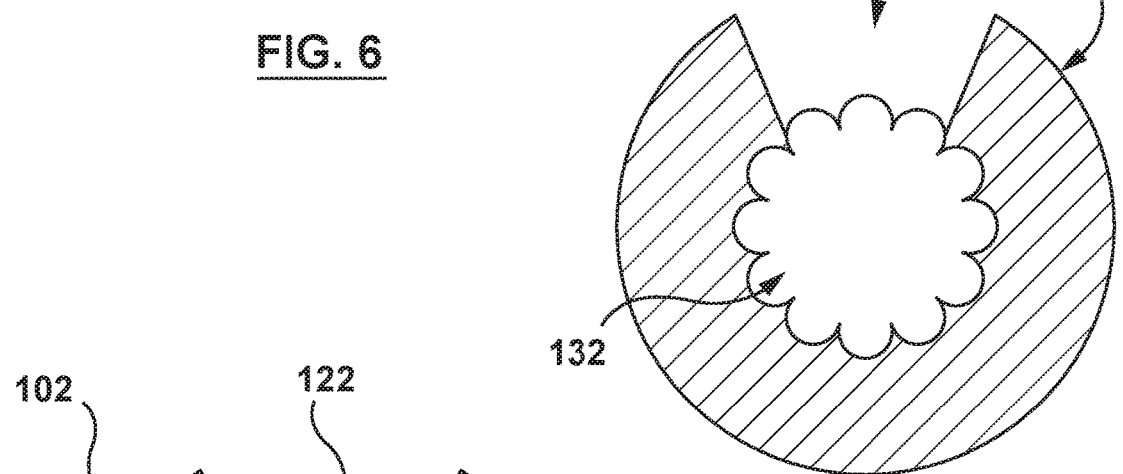
FIG. 7 is a cross-sectional view of the composite wire of FIG. 5 at a step in the method of FIG. 4, wherein the plurality of openings has been provided but the core member has not been processed for removal.

Step 421, shown in FIG. 4 as well as FIG. 7, is to provide the plurality of openings 122 through the outer member 104. The plurality of openings 122 may be laser cut, drilled, etched, or otherwise provided through the outer member 104. Step 421 is not required to be performed after step 411, or before step 431. However, it is preferred for step 421 to be performed before step 431, as the plurality of openings 122 may be utilized as access to the core member 132 for processing, as explained in more detail below. If step 421 is performed after step 411, a cross-section of the composite wire 130 will include the outer member 104, the core member 132, and the opening 122 as shown in FIG. 7.

Step 431 is to remove the core member 132 from the lumen 106 of the outer member 104 without adversely affecting the outer member 104, such as by chemical etching. Step 431 can be performed by any suitable process for removing the core member 132 while preserving the outer member 104. In particular, exposing the composite wire 130 formed from the outer member 104 of MP35N and the core member 132 of molybdenum (Mo) to xenon difluoride (XeF2) gas at low pressure (1-6 Torr) and relatively high temperature (approximately 140° C.) causes the xenon difluoride (XeF2) gas to react with the molybdenum (Mo) core member 132 to form molybdenum fluoride (MoF5) and xenon (Xe) gasses, which can be removed from the lumen 106. Xenon difluoride (XeF2) gas does not react with the outer member 104 formed of MP35N. Accordingly, after step 431 is completed, the outer member 104 remains and the core member 132 has been removed, leaving the cross-sectional structure of the hollow wire 102 shown in FIG. 8. As noted above, the plurality of openings 122 do not need to be formed prior to the step of removing the core member 132 as long as there is a way to expose the core member 132 to the etchant. For example, the ends 126 of the wire may be open or temporary ports may for formed through the outer member 104 to expose the core member 132 to the etchant.

Although a particular embodiment of the outer member 104 made from MP35N, the core member 132 made from molybdenum (Mo), and a xenon difluoride (XeF2) gas etchant has been described, those skilled in the art would recognize that other combinations of materials and etchants may be utilized. For example, and not by way of limitation, the combination of materials and etchants described in the chart below may be utilized. Further, other materials and methods for removing core members may be used, as described, for example, in U.S. Application Publication No. 4011/0008405 to Birdsall et al. and U.S. Application Publication No. 4011/0070358 to Mauch et al., each of which has been previously incorporated by reference.

| Etchant | Outer Member | Core Member |
| --- | --- | --- |
| Xenon-difluoride | Cobalt-chromium alloys (MP35N, MP20N, L605, ELGILOY), Pt—20Ir | Tungsten, molybdenum, niobium, rhenium, carbon, germanium, silicon, Mo—44.5Re |

Step 451 is to fill the lumen 106 of the outer member 104 with the active agent 190. The lumen 106 may be filled by methods known to those skilled in the art. Examples of methods of filling a drug eluting device can be found in U.S. Pat. No. 8,460,745 to Mitchell et al., U.S. Pat. No. 8,381,774 to Mitchell et al., U.S. Pat. No. 8,678,046 to Mitchell et al., U.S. Pat. No. 8,632,846 to Avelar et al., U.S. Pat. No. 8,828,474 to Avelar et al., U.S. Pat. No. 9,549,832 to Peterson et al., and U.S. Pat. No. 9,204,982 to Peterson et al., each of which is herein incorporated by reference in its entirety.

Figure 8:
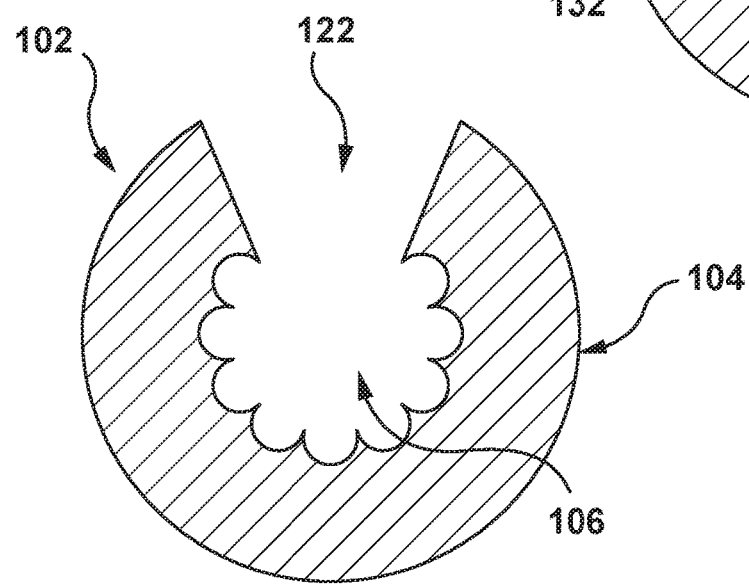
FIG. 8 is a cross-sectional view of the composite wire of FIG. 5 at a step in the method of FIG. 4, wherein the plurality of openings has been provided and the core member has been removed.

FIGS. 9-11 show a method for forming a composite wire 130' for use in embodiments hereof in accordance with another embodiment. The composite wire 130' has an outer member 104' with a first roughness 140' on an inner surface 118' of the outer member 104', and a core member 132' with a second roughness 134' on an outer surface 136', shown schematically in FIG. 8 and in cross-section in FIG. 10. FIGS. 8 and 10 illustrate the composite wire 130' after processing thereof is complete, i.e., after the composite wire 130' is formed as will be described in more detail herein. The outer member 104' with the first roughness 140' forms the hollow wire 102 of the stent 100 after processing thereof to form the stent 100.

The outer member 104' may be any material that is suitable to be used as a stent. The requirements of the outer member 104' are that it be a face-centered cubic (FCC) material, highly ductile, draws well, is biocompatible, is sufficiently resilient to be used as a stent, and that it survives the process of removing the core member 132', as described below. In a non-limiting example, the outer member 104' may be a cobalt-chromium alloy as previously described. As used herein, the term "face-centered cubic (FCC) material" includes materials that have atoms located at each of the corners and the centers of all the cubic faces of the material.

The core member 132' may be any material that is a body-centered cubic (BCC) material, is harder than the outer member 104', deforms transverse to the direction of draw, and that is removed without damaging the outer member 104'. For example, and not by way of limitation, the core member 132' may be tantalum (Ta). As used herein, the term "body-centered cubic (BCC) material" includes materials that have atoms located at each of the corners of a cube and a single atom in the center of the cube.

To form the composite wire 130', the core member 132' is disposed within the outer member 104' as shown in FIG. 9. It will be noted that the inner surface 118' of the outer member 104' and the outer surface 136' of the core member 132' are each smooth at this stage of processing. The outer member 104' and the core member 132' are processed via a drawn filled tubing (DFT) process to form the composite wire 130', as shown in FIG. 10. More precisely, as the outer member 104' and the core member 132' are drawn in a direction along a first longitudinal axis LA1, as best shown in FIG. 9, the body-centered cubic (BCC) core member 132' deforms generally radially outward, or in a direction transverse to the direction of the draw, forming the second roughness 134' on the outer surface 136' of the core member 132'. The magnitude of the deformation may be controlled by the selection of the starting grain size of the material of the body-centered cubic (BCC) core member 132'. For example, a larger starting grain size will result in a greater magnitude of deformation of the second roughness 134'. Simultaneously, as the more ductile, face-centered cubic (FCC) outer member 104' is radially compressed over the harder core member 132', the inner surface 118' of the outer member 104' conforms or molds to the second roughness 134' on the outer surface 146' of the core member 132' to form the corresponding first roughness 140' on the inner surface 118' of the outer member 104'.

In a non-limiting example, the outer member 104' is made of MP35N and the core member 132' is made of tantalum (Ta). The process to remove the core member 132' is exposing the core member 132' to xenon difluoride gas (XeF2), as previously described with respect to composite wire 130 and FIGS. 4-7. Other examples of material combinations of the outer member 104', the core member 132', and the removal method are provided below in chart form.

Although a particular embodiment of an outer member 104' made from MP35N, a core member 132' made from tantalum (Ta), and a xenon difluoride (XeF2) gas etchant has been described, those skilled in the art would recognize other combinations of materials and etchants could be utilized. For example, and not by way of limitation, the combination of materials and etchants described in the chart below may be utilized.

| Etchant | Outer Member | Core Member |
|---|---|---|
| Xenon-difluoride | Cobalt-chromium alloys (MP35N, MP20N, L605, ELGILOY), Pt—20Ir | Tantalum, tungsten, molybdenum, niobium, Ta—2.5W |

Figure 12:
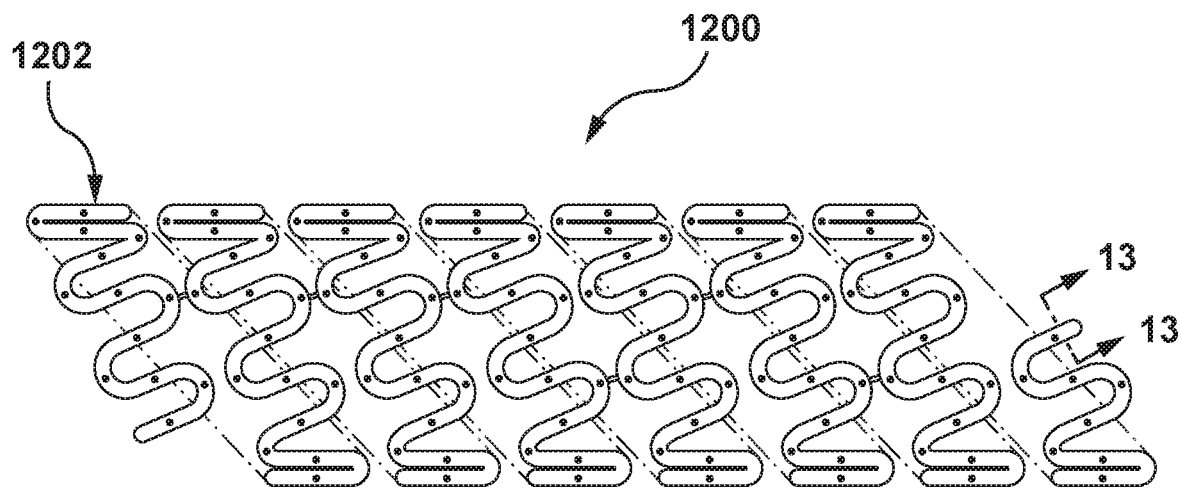
FIG. 12 is a schematic illustration of a stent in accordance with another embodiment hereof, wherein the stent is formed from a hollow wire with a surface area component and an active agent disposed within the lumen of the hollow wire, the surface area component is a roughness forming an increased amount of surface within the lumen of the hollow wire, and the hollow wire includes an intermediate member.
Figure 13:
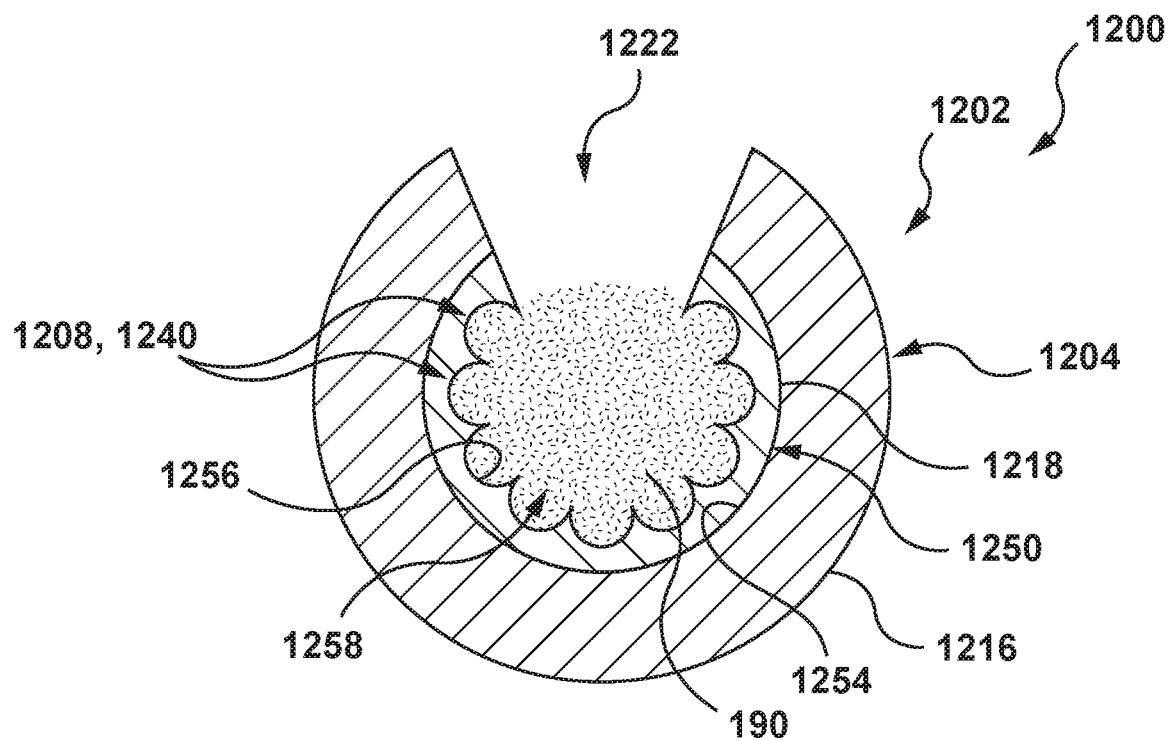
FIG. 13 is a cross-sectional view taken along line 13-13 of FIG. 12.

A stent 1200 in accordance with another embodiment hereof is described herein and is shown in FIGS. 12 and 13. The stent 1200 is formed from a hollow wire 1202. The hollow wire 1202 includes a hollow outer member 1204, a hollow intermediate member 1250 that lines an inner surface 1218 of the outer member 1204, a lumen 1258 defined by an inner surface 1256 of the intermediate member 1250, a plurality of openings 1222, and a surface area component 1208 disposed or formed on the inner surface 1256 of the intermediate ember 1250. In the embodiment of FIGS. 12 and 13 the surface area component 1208 is a roughness 1240 formed on the inner surface 1256 of the intermediate member 1250.

The hollow wire 1202 is formed into the stent 1200, as shown in FIG. 12. The hollow wire 1202 is formed into the stent 1200 in the same manner as the hollow wire 102 is formed into the stent 100 as previously described with respect to FIG. 1. Therefore, construction details and alternatives for forming the hollow wire 1202 into the stent 1200 will not be repeated.

As described above, the hollow wire 1202 includes the outer member 1204 and the intermediate member 1250, as best shown in FIG. 13. The outer member 1204 includes an outer surface 1216 and the inner surface 1218. The intermediate member 1250 includes an outer surface 1254 and the inner surface 1256. The intermediate member 1250 has an outer diameter that is approximately equal to the inner diameter of the outer member 1204. By "approximately equal" it is meant that the outer surface 1254 of the intermediate member 1250 is in contact with the inner surface 1218 of the outer member 1204. The intermediate member 1250 is preferably radiopaque. The radiopaque intermediate member 1250 allows the stent 1200 to be visible under X-ray or fluoroscopic imaging equipment when the outer member 1204, described below, is made of a material that has a radiopacity such that it has poor visibility or is difficult to visualize under X-ray or fluoroscopic imaging equipment. Thus, the radiopaque intermediate member 1250 is more radiopaque than the outer member 1204. The term "radiopaque" refers to the ability of a substance to absorb X-rays. Few substances will transmit 100% of X-rays and few substances will absorb 100% of X-rays. For the purposes of this disclosure, radiopaque will refer to those substances or materials which have suitable visibility for stent procedures when being imaged by an X-ray imaging device such as but not limited to a fluoroscope.

In the embodiment of FIG. 13, the lumen 1258 is defined by or formed within the hollow portion of the intermediate member 1250. The inner surface 1256 of the intermediate member 1250 includes the surface area component 1208, which in the embodiment of FIGS. 12 and 13 is the roughness or roughened texture 1240. In the embodiment of FIGS. 12 and 13, the roughness 1240 of the surface area component 1208 extends longitudinally for the full or entire length of the hollow wire 102. Similar to the surface component 108 previously described with respect to FIGS. 3A and 3B, the surface area component 1208 is configured to increase the amount of surface within the lumen 1258 of the hollow wire 1202 for improved tissue in-growth as previously described herein. While the roughness 1240 is shown with a specific pattern, this is by way of example and not limitation and the roughness 1240 may assume other shapes and or patterns. Moreover, while the hollow wire 1202 is shown as generally having a circular cross-section, the hollow wire 1202 may have other cross-sectional shapes such as, but not limited to a generally elliptical or rectangular cross-section. In some embodiments, the cross-sectional shape and/or size can vary along one or more segments of the hollow wire 1202.

Although the surface area component 1208 has been described herein as extending the entire or full length of the hollow wire 1202 this is by way of example and not limitation. It will be understood that the surface area component 1208 formed on the intermediate member 1250 is similar to the surface area component 108 formed on the outer member 104 previously described herein with respect to FIGS. 1 and 2. The alternative configurations of the surface area component 1208 are the same as those described with respect to the surface area component 108, and thus alternatives of the surface area component 1208 will not be repeated.

In the embodiment of FIG. 13, the active agent 190 (previously described with respect to the embodiment of FIGS. 1 and 2) is deposited within the lumen 1258 of the hollow wire 1202. In the embodiment of FIG. 12, the plurality of openings 1222 provide access to the lumen 1258 to permit the active agent 190 to be released from the lumen 1258. Further, the plurality of openings 1222 provide access to the lumen 1258 to permit tissue in-growth into the lumen 1258 after the active agent 190 has been released from the lumen 1258. The plurality of openings 1222 are similar to the plurality of openings 122 previously described with respect to FIG. 2. However, in the embodiment of FIG. 13, the plurality of openings 1222 extend through the outer member 1204 and the intermediate member 1250 to the lumen 1258.

When the stent 1200 is deployed within a vessel, the active agent 190 elutes from the lumen 1258. Once the active agent 190 has eluted, cells of the vessel adjacent the plurality of openings 1222 migrate through the plurality of openings 1222 and into the lumen 1258 to colonize the lumen 1258. The elution of the active agent 190, migration of cells into the lumen 1258, and coupling of the stent 1200 to the vessel by the colonizing cells to reduce micro-injuries is similar to the elution of the active agent 190, migration of cells into the lumen 106, and coupling of the stent 100 as previously described herein.

Figure 14:
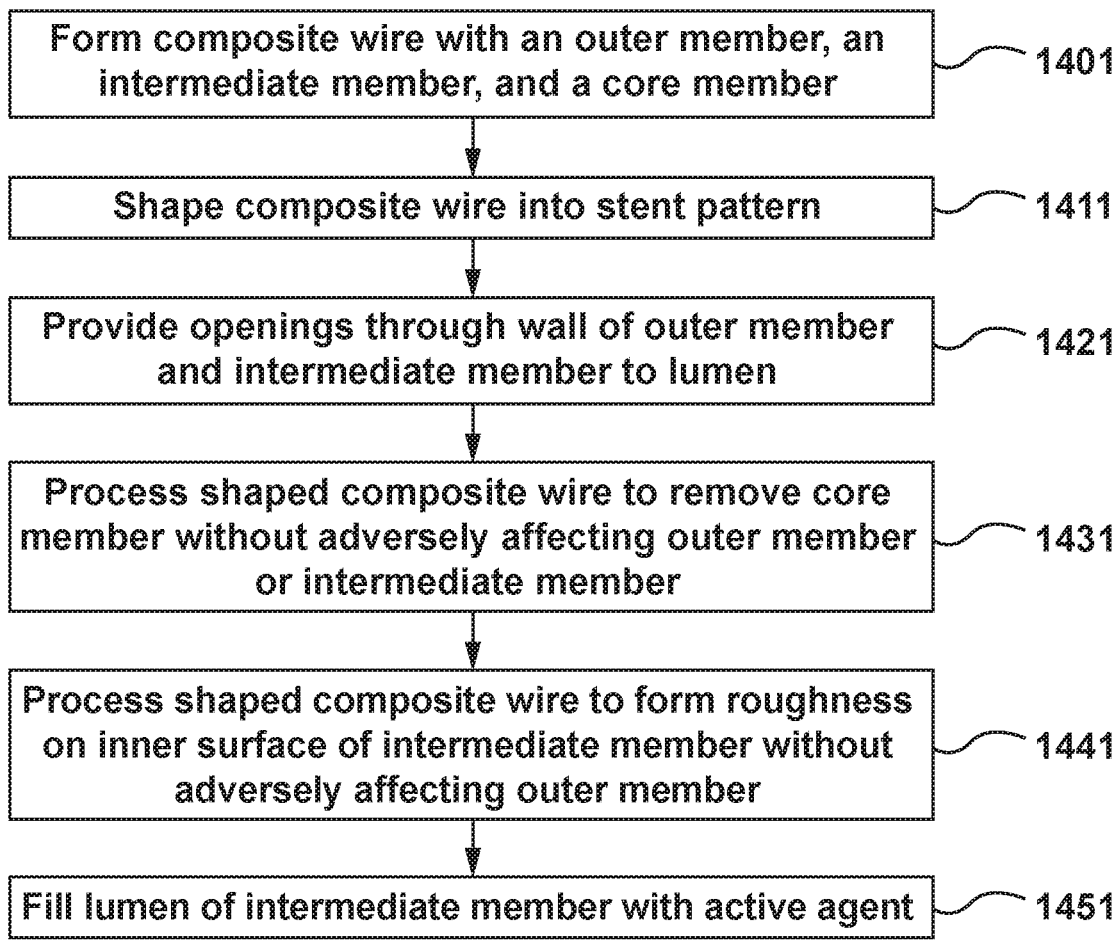
FIG. 14 is flow chart illustrating an embodiment of a method of forming the stent of FIG. 12.

FIGS. 14-19 show a method for forming stent 1200 in accordance with an embodiment hereof. As shown in FIG. 14, step 1401 is to utilize a composite wire 1230 having the outer member 1204, the intermediate member 1250, and a core member 1232, as shown schematically in FIG. 15 and in cross-section in FIG. 16. The outer member 1204 and the intermediate member 1250 form the hollow wire 1202 of the stent 1200 described above with respect to FIGS. 12 and 13 after processing. In the embodiment of FIGS. 14-19, the surface area component 1208 is formed on the intermediate member 1250 after removal of the core member 1232 from the composite wire 1230.

The outer member 1204 may be any material that is suitable to be used as a stent. More specifically, the requirements of the outer member 1204 are that it be biocompatible, sufficiently resilient to be used as a stent, and that it survives the process for eliminating the core member 1232. For example, and not by way of limitation, the outer member 1204 may be a cobalt-chromium alloy, as previously described herein.

Figure 15:
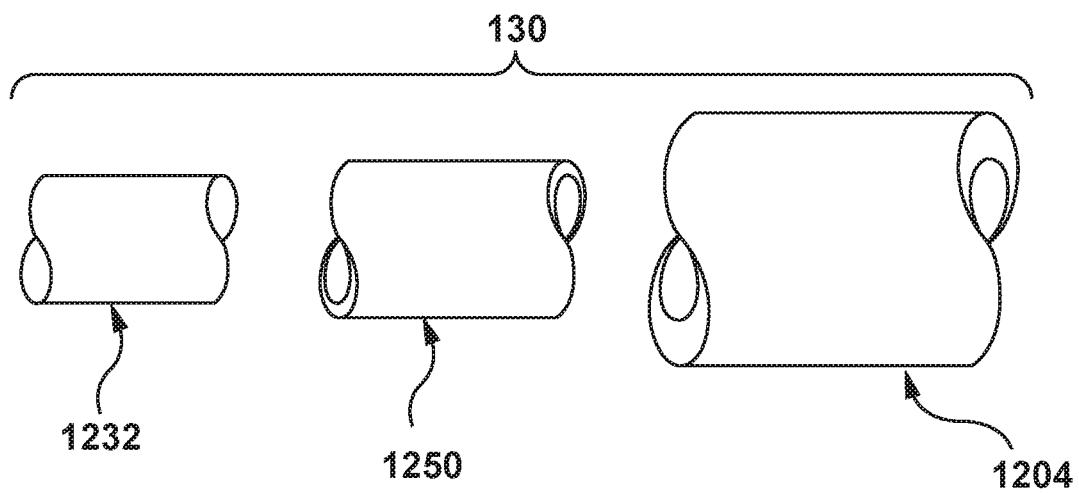
FIG. 15 is a schematic illustration of a composite wire which may be utilized for forming a stent in the method of FIG. 14, the composite wire including an outer member, an intermediated member, a core member, and a surface area component.
Figure 16:
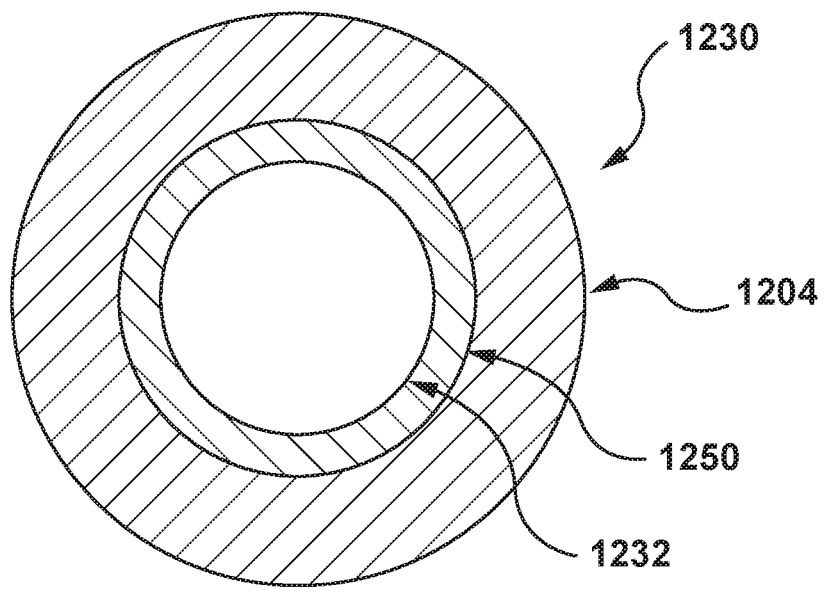
FIG. 16 is a cross-sectional view of the composite wire of FIG. 15 at a step in the method of FIG. 14, wherein the plurality of openings has not been provided and the core member has not been processed for removal.

The intermediate member 1250 may be any material that is suitable for forming a stent. The requirements of the intermediate member 1250 are that it be biocompatible, sufficiently resilient to be used as a stent, and that it survives the process for eliminating the core member 1232, as described in more detail below. As previously stated, the intermediate member 1250 may preferably be a radiopaque material. Accordingly, when the intermediate member 1250 is a radiopaque material, the intermediate member 1250 is more radiopaque than the outer member 1204. Thus, selection of the material for the intermediate member 1250 depends on the material of the outer member 1204, the material of the core member 1232, the process selected for removing the core member 1232 and the process selected to form the roughness 1240 on the inner surface 1256 of the intermediate member 1250. The core member 1232 is a sacrificial material that is removed without damaging the outer member 1204 or the intermediate member 1250. To form the composite wire 1230, the core member 1232 is disposed within the intermediate member 1250 and the intermediate member 1250 is disposed within the outer member 1204, as shown in FIGS. 15 and 16. The composite wire 1230 may be formed by any processing method known in the art, for example and not by way of limitation, a co-drawing process, extrusion, cladding, or any other suitable method. Stated another way, the composite wire 1230 may be formed by methods of forming composite wires known to those skilled in the art.

In a non-limiting example, the outer member 1204 is made of MP35N, the intermediate member 1250 is made of tantalum (Ta), the core member 1232 is made of silver (Ag), the etching process to remove the core member 1232 is exposing the core member 1232 to nitric acid (HNO3) as will be explained in more detail below, and the etching process to form the roughness 1240 on the inner surface 1256 of the intermediate member 1250 is exposing the intermediate member 1250 to hydrofluoric acid (HF) as will be explained in more detail below. Other examples of material combinations of the outer member 1204, the intermediate member 1250, the core member 1232, and the etching agents are provided below in chart form.

Referring back to FIG. 14, step 1411 is to shape the composite wire 1230 into the stent pattern. Step 1411 is the same as step 411 previously described herein with respect to FIGS. 3-7. As discussed above, the stent pattern can be the pattern shown in FIG. 12 or any other suitable pattern formed from a wire.

Figure 17:
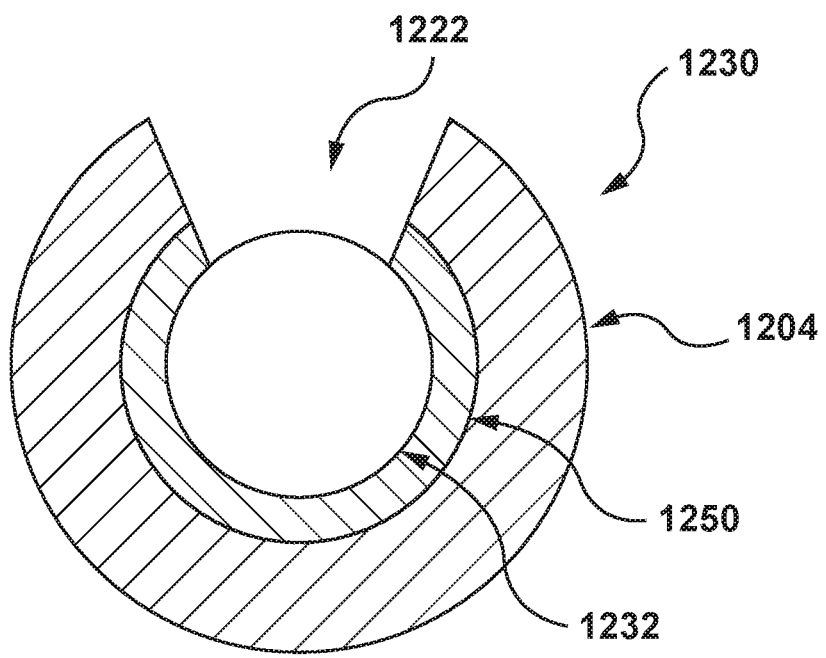
FIG. 17 is a cross-sectional view of the composite wire of FIG. 15 at a step in the method of FIG. 14, wherein the plurality of openings has been provided but the core member has not been processed for removal.
Figure 18:
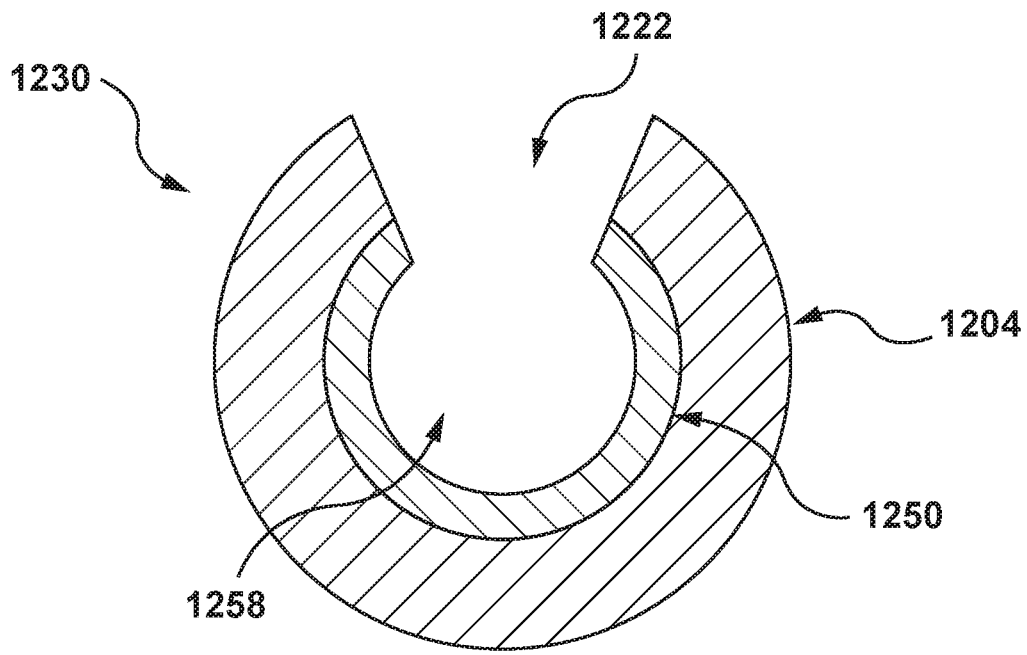
FIG. 18 is a cross-sectional view of the composite wire of FIG. 15 at a step in the method of FIG. 14, wherein the plurality of openings has been provided and the core member has been removed.
Figure 19:
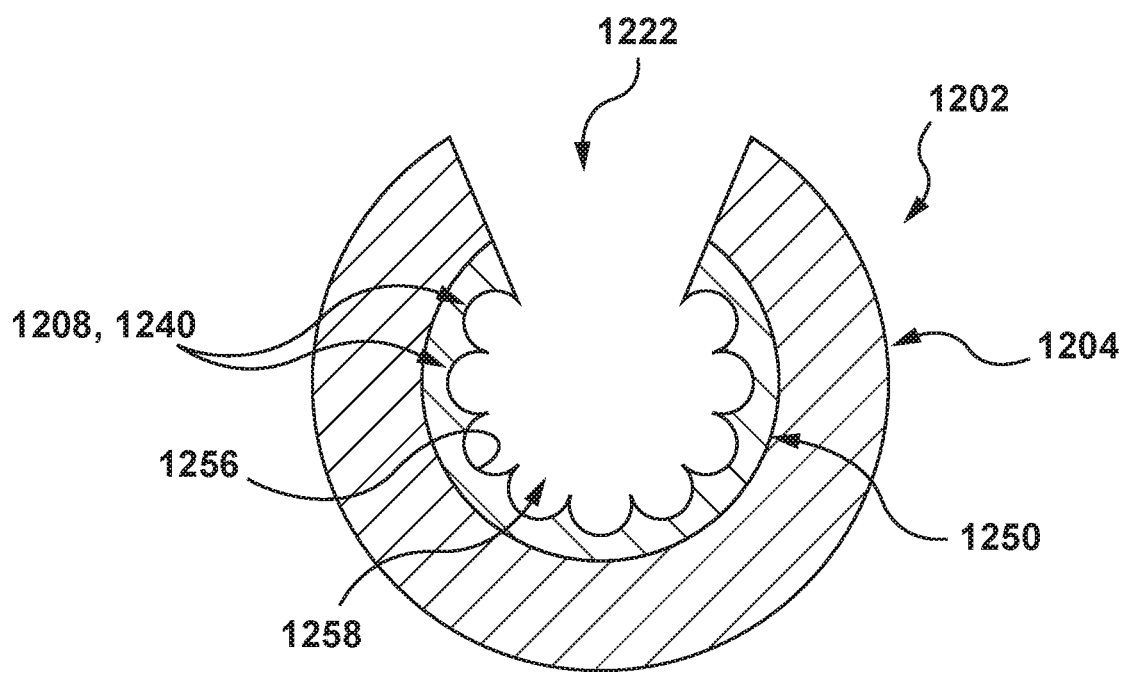
FIG. 19 is a cross-sectional view of the composite wire of FIG. 15 at a step in the method of FIG. 14, wherein the plurality of openings has been provided, the core member has been removed, and the surface area component has been formed.

Step 1421, shown in FIG. 14, is to provide the plurality of openings 1222 through the outer member 1204 and the intermediate member 1250. The plurality of openings 1222 may be formed as previously described with respect to the plurality of openings 122 of FIGS. 3-7. If step 1421 is performed after step 1411, a cross-section of the composite wire 1230 will include the outer member 1204, the intermediate member 1250, the core member 1232, and an opening 1222, as shown in FIG. 17.

Step 1431 is to remove the core member 1232 from the lumen 1258 of the intermediate member 1250 such as by chemical etching. The removal of the core member 1142 is accomplished without adversely affecting the outer member 1204 or the intermediate member 1250. Step 1431 can be performed by any suitable process for removing the core member 1232 while preserving the outer member 1204 and the intermediate member 1250. In a non-limiting example, exposing the composite wire 1230 formed from the outer member 1204 of MP35N, the intermediate member 1250 of tantalum (Ta), and the core member 1232 of silver (Ag) to nitric acid (HNO3) causes the nitric acid (NAO3) to react with the silver (Ag) core member 1232 to form silver nitrate (AgNO3), water (H20) and nitrous dioxide (NO2), which can be removed from the lumen 1258. Nitric acid (HNO3) does not react with the outer member 1204 formed of MP35N or the intermediate member 1250 formed of tantalum (Ta). Accordingly, after step 1431 is completed, the outer member 1204 and the intermediate member 1250 remain but the core member 1232 has been removed, forming the lumen 1258 and leaving the cross-sectional structure shown in FIG. 18. As noted previously, the plurality of openings 1222 do not need to be formed prior to the step of removing the core member 1232 as long as there is a way to expose the core member 1232 to the etchant.

Step 1441 is to form the surface area component 1208 (i.e., the roughness 1240 on the inner surface 1256 of the intermediate member 1250) without adversely affecting the outer member 1204. Step 1441 is performed after step 1431 by any suitable process that forms the roughness 1240 on the inner surface 1256 of the intermediate member 1250 while preserving the outer member 1204. In a non-limiting example, the surface area component 1208 is formed by chemical etching. More particularly, the composite wire 1230, which at this stage includes only the outer member 1204 of MP35N and the intermediate member 1250 of tantalum (Ta), is exposed to hydrofluoric acid (HF). The hydrofluoric acid (HF) reacts with the tantalum (Ta) to remove a portion of the inner surface 1256 of the intermediate member 1250 to form the roughness 1240 on the inner surface 1256 of the intermediate member 1250. The pattern and/or magnitude of the roughness 1240 may be varied by selection of the material, the initial grain size, and the pre-existing surface texture of the intermediate member 1250. Hydrofluoric acid (HF) does not react with the outer member 1204 formed of MP35N and thus the outer member 1204 is not adversely affected by the use thereof. Accordingly, after step 1441 is completed, the hollow wire 1202 is formed. The hollow wire 1202 includes the outer member 1204 and the remaining portion of the intermediate member 1250, as shown in cross-sectional structure in FIG. 19.

While described herein with separate steps 1431 and 1441, in another embodiment, step 1431 and step 1441 may be performed simultaneously. In an example, nitric acid (HNO3) and hydrofluoric acid (HF) may be combined and the composite wire 1230 exposed to the acid combination to remove the core member 1232 and to form or etch the roughness 1240 onto the inner surface 1256 of the intermediate member 1250 simultaneously. When performed simultaneously, the nitric acid and the hydrofluoric acid are selected such that the core member 1232 is removed and the roughness 1240 is formed on the inner surface 1256 of the intermediate member 1250. More specifically, the concentration of the nitric acid and the concentration of the hydrofluoric acid is selected and the composite wire 1230 exposed for sufficient time to completely remove the core member 1232 from the lumen 1258 but only remove or etch a small amount of the inner surface 1256 of the intermediate member 1250 to form the roughness 1240. The concentration of each acid is selected such that the core member 1232 is etched and removed at a faster rate than the intermediate member 1250. Because the intermediate member 1250 is etched and removed at a slower rate than the core member 1232, only a portion of the intermediate member 1250 is etched and removed, forming the roughness 1240, because the etchant (hydrofluoric acid) does not have sufficient exposure time to completely etch and remove the intermediate member 1250 Accordingly, after simultaneously performed steps 1431 and 1441 are completed, the outer member 1204 remains, the intermediate member 1250 with the roughness 1240 on the inner surface 1256 remains, and the core member 1232 has been removed, forming the lumen 1258 and leaving the cross-sectional structure shown in FIG. 19.

Although an embodiment of the outer member 1204 made from MP35N, the intermediate member 1250 made from tantalum (Ta), the core member 542 made from silver (Ag), and nitric acid (HNO3) and hydrofluoric acid (HF) etchants has been described, those skilled in the art will understand that other combinations of materials and etchants could be utilized. For example, and not by way of limitation, the combination of materials and etchants described in the chart below may be utilized. Further, other materials and methods for removing core members may be used, as previously described.

| Outer Member | Intermediate Member | Core Member | Core Etchant | Intermediate Etchant |
|---|---|---|---|---|
| Cobalt-chromium alloys (MP35N, MP20N, L605, ELGILOY), Nitinol, Titanium, Titanium alloys | Tantalum, Ta—2.5W | Copper, Silver, Zn, Mg | Nitric or sulfuric acid | Nitric & HF |

Step 1451 is to fill the lumen 1258 of the intermediate member 1250 with the biologically or pharmacologically active agent 190. Step 1451 of FIG. 14 is the same as step 451 of FIG. 4 previously described.

With an understanding of the example of the surface area component 108 of the hollow wire 102 of FIGS. 1-8, it will be understood that the surface area component 108 may be configured with other shapes and disposed at other locations of the hollow wire 102. FIGS. 20-23 show various embodiments of shapes and distribution of surface area components within the lumen of a hollow wire. Although such surface area components are shown as formed on the inner surface of an outer member of the hollow wire, it will be understood by those of ordinary skill in the art that any such surface area components may alternatively be formed on the inner surface of an intermediate member similar to intermediate member 1250 described above. Further, various modifications to the size, shape, number and specific distribution of surface area components illustrated in FIGS. 20-23 may be made within the scope of the present invention. The surface area components of all embodiments described herein may be utilized together in any combination with the specific configuration optimized for specific treatment purposes.

Figure 20:
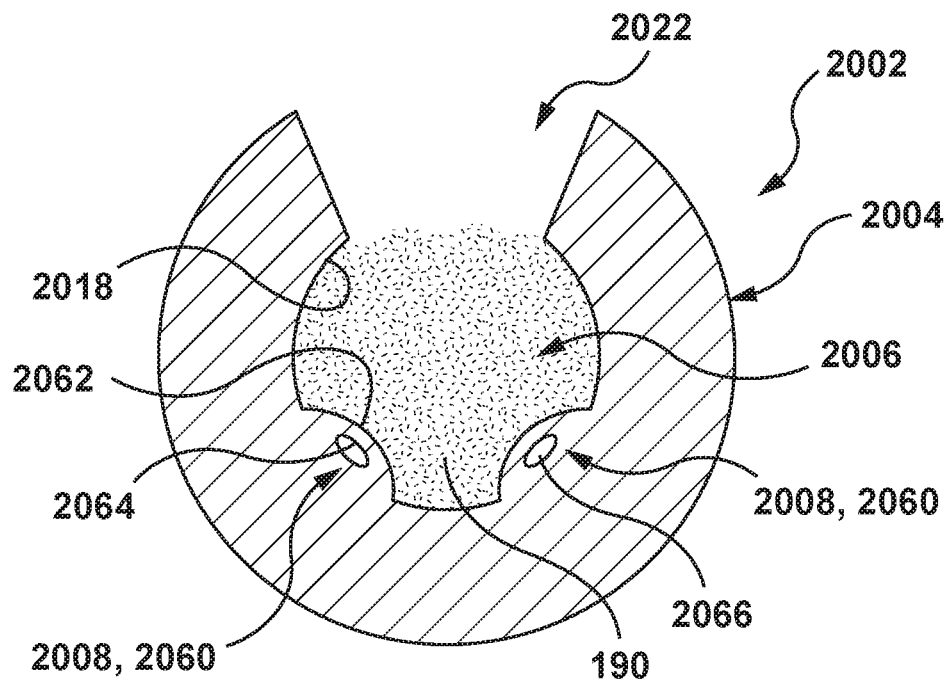
FIG. 20 is a cross-sectional view taken along line 2-2 of FIG. 1, wherein the stent includes a plurality of surface area components in accordance with another embodiment hereof, wherein each surface area component is a channel forming an increased amount of surface within the lumen of the hollow wire.

FIG. 20 shows a cross-sectional view of a hollow wire 2002 with an example of a plurality of surface area components 2008 according to another embodiment hereof. In the embodiment of FIG. 20, an inner surface 2018 of an outer member 2004 includes two (2) surface area components 2008 disposed thereon, with each surface area component 2008 being a channel 2060. Each channel 2060 is a tubular protrusion extending radially inward from the inner surface 2018 of the outer member 2004 and includes an outer surface 2062 and an inner surface 2064. The inner surface 2064 of the channel 2060 defines or forms a channel lumen 2066. Each channel 2060 is configured to increase the amount of surface within a lumen 2006 of the hollow wire 2002 for improved tissue in-growth as described in more detail below.

In the embodiment of FIG. 20, each channel 2060 is discontinuous and starts and stops along the length of the hollow wire 2002 to form distinct segments of surface area components 2008 along the length of the hollow wire 2002. Channels 2060 are circumferentially spaced around the inner surface 2018 of the outer member 2004. Each channel 2060 may be formed as a portion of the outer member 2004 through a process such as, but not limited to extrusion, or may alternatively be formed as a separate component and coupled to the inner surface 2018 of the outer member 2004 by methods such as, but not limited to adhesives, fusing, welding, or any other suitable method. While FIG. 20 illustrates each channel 2060 as extending generally longitudinally along the inner surface 2018 of the outer member 2004, this is by way of example and not limitation, and each channel 2060 may extend in other paths along the inner surface 2018 of the outer member 2004. For example, each channel 2060 may extend in a helical path along the inner surface 2018 of the outer member 2004 or in a circumferential path along the inner surface 2018 of the outer member 2004.

While shown with two (2) channels 2060 at specific locations within the lumen 2006, this is by way of example and not limitation, and it will be understood that a greater or lesser number of channels may be utilized at any location along the inner surface 2018 of the outer member 2004. Additionally, although each channel 2060 is shown with a specific shape, this too is by way of example and not limitation, and each channel 2060 may assume other shapes, and different shapes may be combined in any combination.

When a stent is formed from the hollow wire 2002 and deployed within a vessel, the active agent 190 elutes from the lumen 2006 of the stent. Once the active agent 190 has been eluted, cells originating from the vessel migrate through a plurality of openings 2022 and into the lumen 2006. The cells attach or couple to the surfaces within the lumen 2006. More specifically, the cells couple to the inner surface 2018 of the outer member 2004, to the outer surface 2062 of each channel 2060, and to the inner surface 2064 of each channel 2060. The cells migrate to the channel lumen 2066 via the breaks or gaps between segments of the channels 2060. Once attached thereto, the cells grow or colonize and form an extracellular matrix to couple the stent to the vessel as previously described herein.

While described herein with each channel 2060 as a discontinuous segment that starts and stops along the length of the hollow wire 2002 to form distinct segments of surface area components 2008 along the length of the hollow wire 2002, in an alternative embodiment each channel 2060 is a continuous channel extending the full length of the hollow wire 2002. In this alternate embodiment, each continuous channel 2060 further includes at least one opening or hole to provide access to the channel lumen 2066 for tissue in growth.

Figure 21:
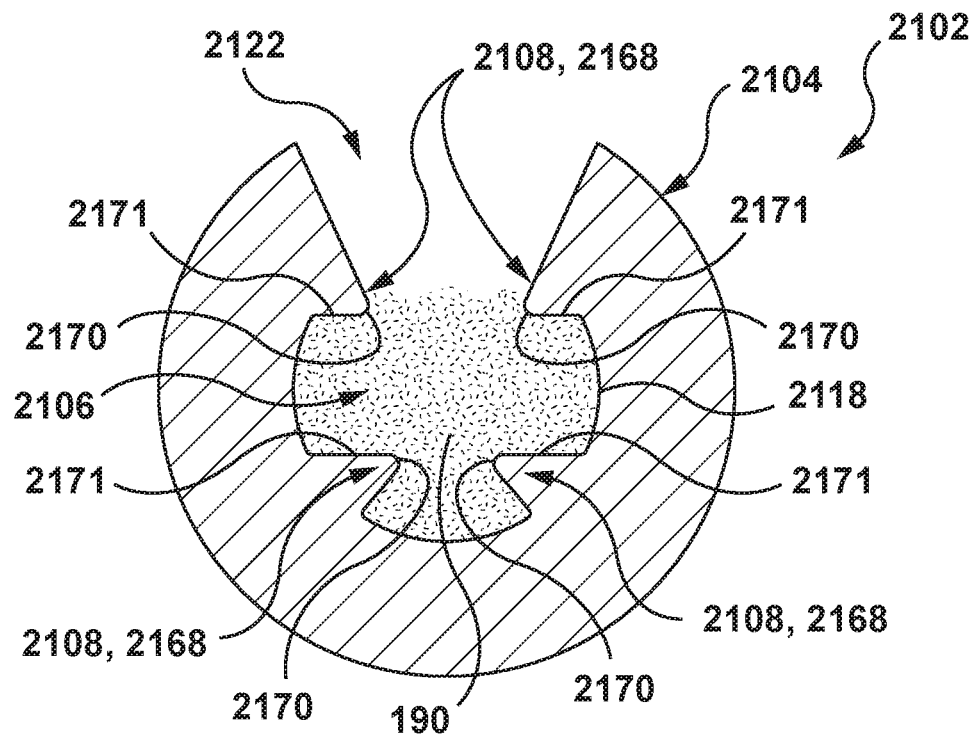
FIG. 21 is a cross-sectional view taken along line 2-2 of FIG. 1, wherein the stent includes a plurality of surface area components in accordance with another embodiment hereof, wherein each surface area component is a ledge forming an increased amount of surface within the lumen of the hollow wire.

FIG. 21 shows a cross-sectional view of a hollow wire 2102 with an example of a plurality of surface area components 2108 according to another embodiment hereof. The embodiment of FIG. 21 includes four (4) surface area components 2108 disposed on an inner surface 2118 of an outer member 2104. Each surface area component 2108 is a ledge 2168 extending a full length of the hollow wire 2102. Each ledge 2168 includes a planar extension extending from the inner wall 2118 of the outer member 2104 into a lumen 2106 and includes an outer surface 2170. More particularly, each ledge 2168 includes a planar or flat portion 2171 on the outer surface 2170. The planar orientation of each ledge 2168 is configured to improve the distribution and to increase the amount of surface within the lumen 2106 of the hollow wire 2102 to improve the distribution of the tissue in-growth to reduce micro-injuries associated with tensile loads created by biomechanical motion of the vessel as described in more detail below.

Ledges 2168 are circumferentially spaced around the inner surface 2118 of the outer member 2104. Each ledge 2168 may be formed as a portion of the outer member 2104 through a process such as, but not limited to a co-drawing process, extrusion, cladding, or any other suitable method. For example, the plurality of ledges 2168 on the inner surface 2118 of the outer member 2104 may be formed through a drawn filled tubing (DFT) process similar to the process forming the first roughness 140 on the inner surface 118 of the outer member 104 previously described with reference to FIGS. 4-8. Alternatively, each ledge 2168 may be formed as a separate component and coupled to the inner surface 2118 of the outer member 2104 by methods such as, but not limited to adhesives, fusing, welding, or any other suitable method. While FIG. 21 illustrates each ledge 2168 as extending generally longitudinally along the inner surface 2118 of the outer member 2104 for the full or entire length of the hollow wire 2102, this is by way of example and not limitation, and each ledge 2168 may extend in other paths as previously described with respect to the channel 2060 of FIG. 20. Additionally, each ledge 2168 may be discontinuous and start and stop along the length of the hollow wire 2102 to form segments of the surface area component 2108 along the length of the hollow wire 2102. Further, the segments of the surface area component 2108 may be positioned at select portions or locations of a stent formed from the hollow wire 2102 such as one or more crowns 2112 (not shown in FIG. 21), one or more struts 2110 (not shown in FIG. 21), or any combination thereof to encourage preferred tissue in-growth in select locations. In another embodiment, the segments of the surface area component 2108 may be positioned at the end portions of the stent.

While shown with four (4) ledges 2168, this is by way of example and not limitation, and a greater or lesser number of ledges 2168 may be utilized. Additionally, although each ledge 2168 is shown at a specific location within the lumen 2106, it will be understood that each ledge 2168 may be disposed at any location along the inner surface 2118 of the outer member 2104. Even further, while each ledge 2168 is shown with a specific shape, this too is by way of example and not limitation, and each ledge 2168 may assume other shapes and that ledges 2168 of different shapes may be utilized in any combination.

When a stent is formed from the hollow wire 2102 and deployed within a vessel, the stent elutes the active agent 190. Once the active agent 190 has been eluted, cells originating from the vessel migrate through the plurality of openings 2122 and into the lumen 2106. The cells attach or couple to the surfaces within the lumen 2106. More specifically, the cells couple to the inner surface 2118 of the outer member 2104 and to the outer surface 2170 of each ledge 2168. Once attached thereto, the cells grow or colonize and form an extracellular matrix to couple the stent to the vessel as previously described.

Figure 22:
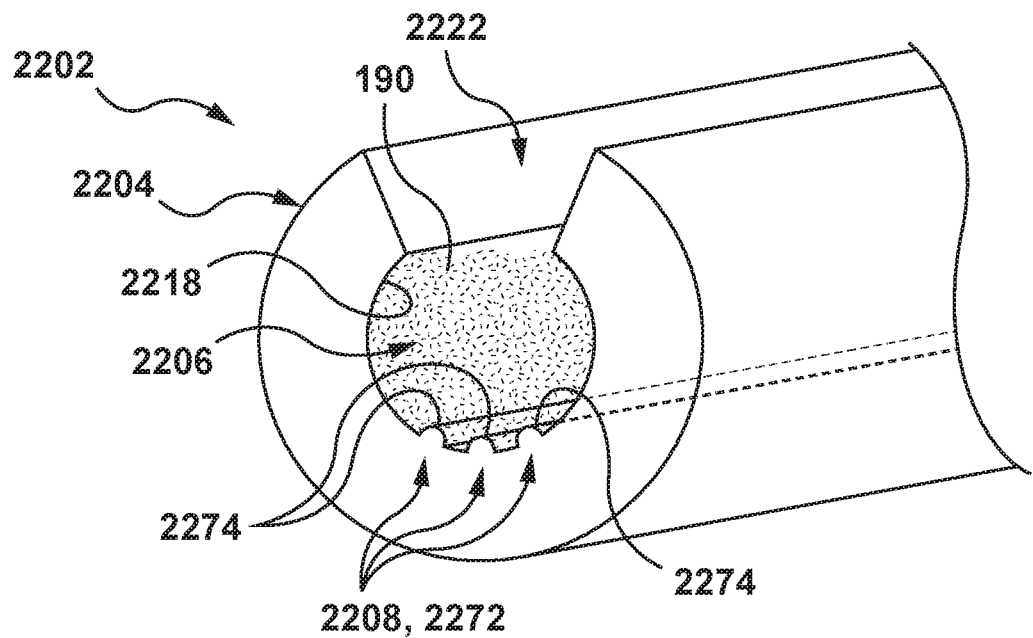
FIG. 22 is a cross-sectional view taken along line 2-2 of FIG. 1, wherein the stent includes a plurality of surface area components in accordance with yet another embodiment hereof, wherein each surface area component is a longitudinal protrusion forming an increased amount of surface within the lumen of the hollow wire.

FIG. 22 shows a cross-sectional view of a hollow wire 2202 with an example of a plurality of surface area components 2208 according to yet another embodiment hereof. In the embodiment of FIG. 22, an inner surface 2218 of an outer member 2204 includes three (3) surface area components 2208. Each surface area component 2208 is a rounded protrusion 2272 extending radially inward and includes an outer surface 2274. Each outer surface 2274 is rounded such that the outer surface 2274 does not include a planar or flat portion. Each protrusion 2272 is configured to increase the amount of surface within a lumen 2206 of the hollow wire 2202 to improve the distribution of tissue in-growth to reduce micro-injuries associated with tensile loads created by biomechanical motion of the vessel as described in more detail below.

In the embodiment of FIG. 22, each protrusion 2272 extends longitudinally within the lumen 106 for a full length of the hollow wire 2202. Protrusions 2272 are circumferentially spaced around the inner surface of outer member 2204. Each protrusion 2272 may be formed as a portion of the outer member 2204 through a process such as, but not limited to a co-drawing process, extrusion, cladding, or any other suitable method. For example, the plurality of protrusions 2272 on the inner surface 2218 of the outer member 2204 may be formed through a drawn filled tubing (DFT) process similar to the process forming the first roughness 140 on the inner surface 118 of the outer member 104 previously described with reference to FIGS. 4-8. Alternatively, each protrusion 2272 may be formed as a separate component and coupled to the inner surface 2218 of the outer member 2204 by methods such as, but not limited to adhesives, fusing, welding, or any other suitable method. In the embodiment of FIG. 22, each protrusion 2272 is shown as extending longitudinally along the inner surface 2218 of the outer member 2204. However, this is by way of example and not limitation, and each protrusion 2272 may extend in other paths such as helically or circumferentially, as previously described with respect to the channel 2060 of FIG. 20. Further, while described as extending the full length of the hollow wire 2202, each protrusion 2272 may be discontinuous and start and stop along the length of the hollow wire 2202 to form segments of the surface area component 2208 along the length of the hollow wire 2202. Further, the segments of the surface area component 2208 may be positioned at select portions or locations of a stent formed from the hollow wire 2202 such as one or more crowns 2212 (not shown in FIG. 22), one or more struts 2210 (not shown in FIG. 22), or any combination thereof to encourage preferred tissue in-growth in select locations. In another embodiment, the segments of the surface area component 2208 may be positioned at the end portions of the stent.

While shown with three (3) protrusions 2272 at specific locations, this is by way of example and not limitation, and a greater or lesser number of protrusions 2272 may be utilized with each protrusion 2272 positioned at any location along the inner surface 2218 of the outer member 2204. Even further, while each protrusion 2272 is shown with a specific shape and size, this too is by way of example and not limitation, and each protrusion 2272 may assume other shapes and sizes, and that protrusions 2272 of different shapes and sizes may be utilized in any combination.

When a stent is formed from hollow wire 2202 and deployed within a vessel, the stent elutes the active agent 190. Once the active agent 190 has been eluted, cells originating from the vessel migrate through a plurality of openings 2222 and into the lumen 2206. The cells attach or couple to the surfaces within the lumen 2206. More specifically, the cells couple to the inner surface 2218 of the outer member 2204 and to the outer surface 2274 of each protrusion 2272. Once attached thereto, the cells grow or colonize and form an extracellular matrix to couple the stent to the vessel as previously described.

Figure 23:
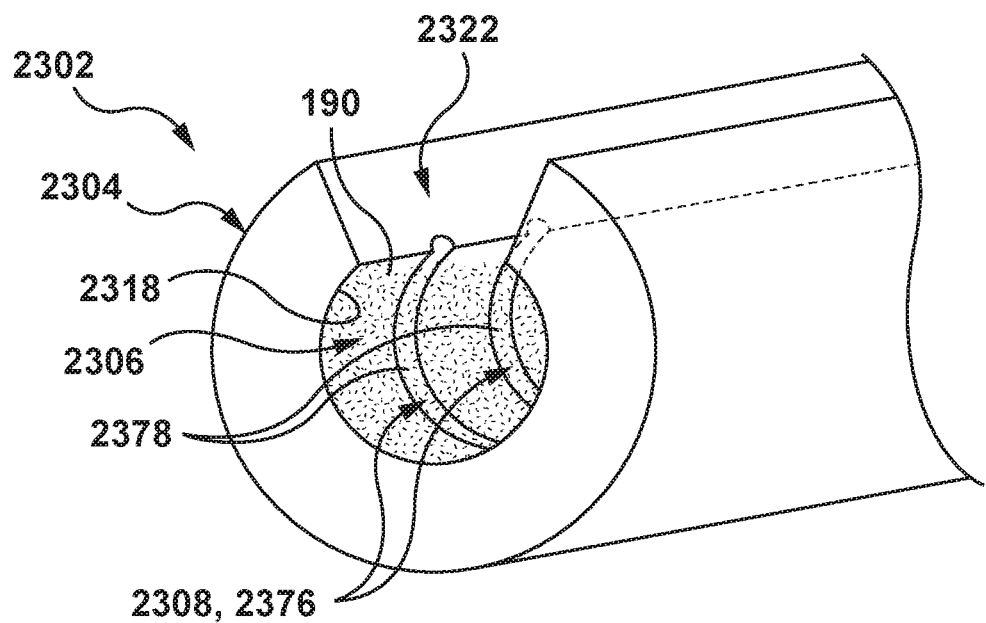
FIG. 23 is a cross-sectional view taken along line 2-2 of FIG. 1, wherein the stent includes a plurality of surface area components in accordance with another embodiment hereof, wherein each surface area component is a radial groove forming an increased amount of surface within the lumen of the hollow wire.

FIG. 23 shows a cross-sectional view of a hollow wire 2302 with an example of a plurality of surface area components 2308 according to yet another embodiment hereof. In the embodiment of FIG. 23, an inner surface 2318 of an outer member 2304 includes two (2) surface area components 2308. Each surface area component 2308 is a channel or groove 2376 extending radially outward and includes an inner surface 2378. Each groove 2376 is configured to increase the amount of surface within a lumen 2306 of the hollow wire 2302 to improve the distribution of tissue in-growth to reduce micro-injuries associated with tensile loads created by biomechanical motion of the vessel as described in more detail below.

In the embodiment of FIG. 23, each groove 2376 extends circumferentially within the lumen 2306 for the entire or full length of the hollow wire 2302. Grooves 2376 are longitudinally or axially spaced apart along the length of the hollow wire 2302. Each groove 2376 may be formed by other methods such as, but not limited to a co-drawing process, a co-drawing process, extrusion, cladding, machining, laser ablation, chemical etching, or any other suitable method. For example, the plurality of grooves 2276 may be formed through a drawn filled tubing (DFT) process similar to the process forming the first roughness 140 on the inner surface 118 of the outer member 104 previously described with reference to FIGS. 4-8. While each groove 2376 is shown as extending circumferentially along the inner surface 2318 of the outer member 2304, this is by way of example and not limitation, and each groove 2376 may extend in other paths, such as longitudinally or helically, as previously described with respect to the channel 2060 of FIG. 20. Additionally, although described as extending the full length of the hollow wire 2302, each groove 2376 may be discontinuous and start and stop along the length of the hollow wire 2302 to form segments of the surface area component 2308 along the length of the hollow wire 2302. Further, the segments of the surface area component 2308 may be positioned at select portions or locations of a stent formed from the hollow wire 2302 such as one or more crowns 2312 (not shown in FIG. 23), one or more struts 2310 (not shown in FIG. 23), or any combination thereof to encourage preferred tissue in-growth in select locations. In another embodiment, the segments of the surface area component 2308 may be positioned at the end portions of the stent.

While shown with two (2) grooves 2376 at specific locations, this is by way of example and not limitation, and a greater or lesser number of grooves 2376 may be utilized with each groove 2376 positioned at any location along the inner surface 2318 of the outer member 2304. Even further, while each groove 2376 is shown with a specific size and shape or cross-sectional profile, this too is by way of example and not limitation, and each groove 2376 may assume other sizes and shapes. Further, grooves 2376 of different sizes and shapes may be utilized in any combination.

When a stent is formed from the hollow wire 2302 and deployed within a vessel, the stent elutes the active agent 190. Once the active agent 190 has been eluted, cells originating from the vessel migrate through a plurality of openings 2322 and into the lumen 2306. The cells attach or couple to the surfaces within the lumen 2306. More specifically, the cells couple to the inner surface 2318 of the outer member 2304 and to the inner surface 2378 of each groove 2376. Once attached thereto, the cells grow or colonize and form an extracellular matrix to couple the stent to the vessel as previously described.

In the embodiments of FIGS. 1-23, a surface area component is disposed within a lumen of a hollow wire to increase the amount of surface available for tissue-ingrowth within the hollow wire. However, the surface area component may additionally and/or alternatively be disposed within at least one opening of the hollow wire to increase the amount of surface within the hollow wire. Accordingly, the following embodiments of FIGS. 24-28 describe a surface area component disposed within at least one opening of the hollow wire. While described separately, it will be understood that surface area components within the lumen and surface area components within the plurality of openings may be combined in any combination to increase the amount of surface within the corresponding hollow wire.

Figure 24:
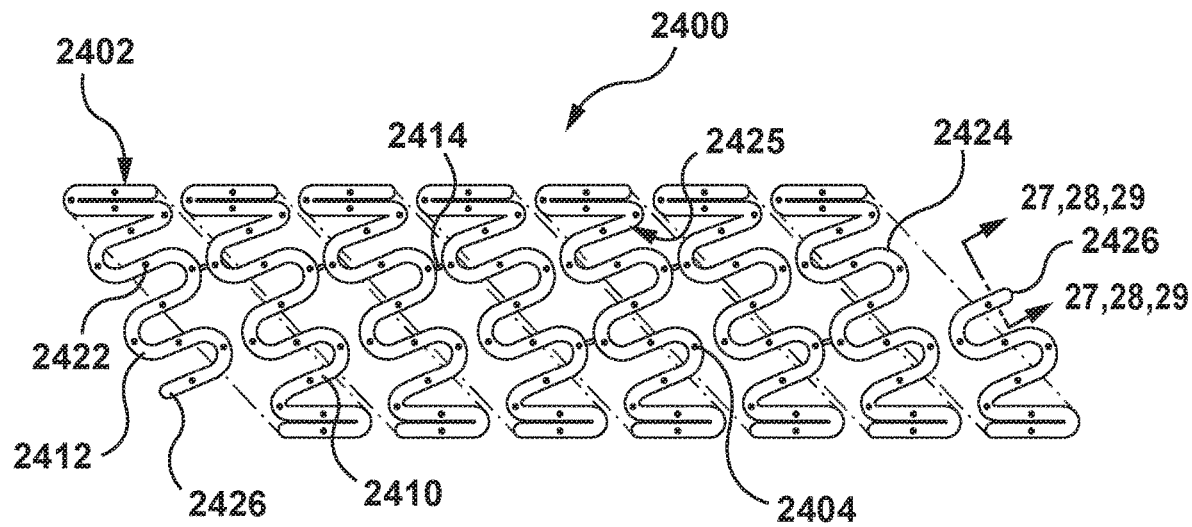
FIG. 24 is a schematic illustration of a stent in accordance with an embodiment hereof, wherein the stent is formed from a hollow wire with a surface area component disposed on a radial surface within at least one opening and an active agent disposed within a lumen of the hollow wire, wherein the surface area component is a roughness forming an increased amount of surface within the plurality of openings of the hollow wire.
Figure 25:
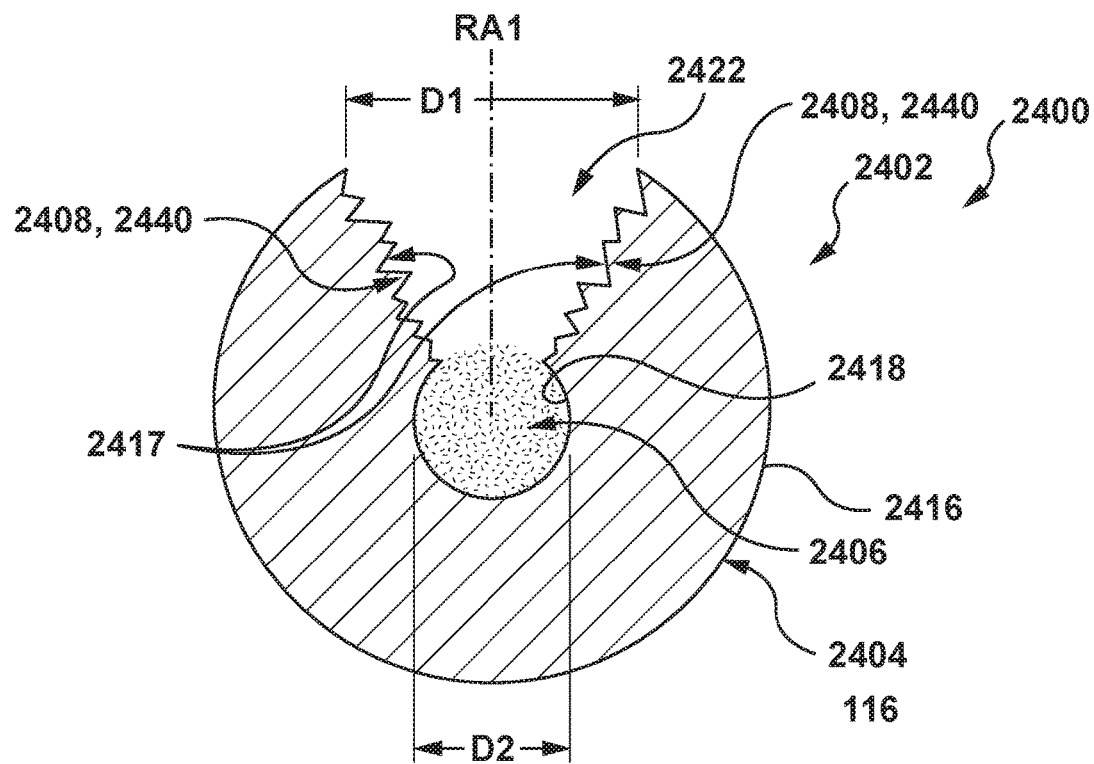
FIG. 25 is a cross-sectional view taken along line 25-25 of FIG. 24.

A stent 2400 in accordance with an embodiment hereof is described herein and shown in FIGS. 24-26. The stent 2400 is formed from a hollow wire 2402. The hollow wire 2402 includes an outer member 2404, a lumen 2406 defined by an inner surface 2418 of the outer member 2404 and extending longitudinally within the outer member 2404. The hollow wire 2402 further includes a plurality of openings 2422. In the embodiment of FIG. 24, the hollow wire 2402 is formed into a series of generally sinusoidal waveforms including generally straight segments or struts 2410 joined by bent segments or crowns 2412. The waveform is helically wound to form the stent 2400 into a generally tubular configuration. In the embodiment shown in FIG. 24, selected crowns 2412 of longitudinally adjacent sinusoids may be joined by, for example, fusion points 2414. However, the invention is not limited to the pattern or configuration shown in FIG. 24. The hollow wire 2402 of the stent 2400 can be formed into any pattern suitable for use as a stent as previously described herein.

Each opening 2422 of the plurality of openings 2422 is defined or formed by a radial surface 2417 of the outer member 2404 extending through the outer member 2404 to the lumen 2406. In the embodiment of FIG. 25, each opening 2422 includes a first diameter D1 at the outer surface 2416 of the outer member 2404. In the embodiment of FIG. 25, the first diameter D1 of the opening 2422 is greater than a second diameter D2 of the lumen 2406 as shown in FIG. 25. Each opening 2422 extends from the outer surface 2416 of the outer member 2404 to the lumen 2406 and may be formed by methods such as, but not limited to machining, laser ablation, chemical etching, or other methods suitable for the purposes described herein. While described herein with the first diameter D1 being greater than the second diameter D2, this is by way of example and not limitation, and in an alternative embodiment, the first diameter D1 may be equal to or less than the second diameter D2. Additionally, while described as extending through the outer member 2404 to the lumen 2406, this too is by way of example and not limitation, and each opening 2422 may extend any desired distance from the outer member 2404 including extending through the hollow wire 2402 from the outer surface 2416 of the outer member 2404 to the opposite outer surface 2416 of the outer member 2404.

At least one opening 2422 includes a surface area component 2408. In the embodiment of FIGS. 24-26B, the surface area component 2408 is a roughness 2440 disposed or formed on the radial surface 2417 of the outer member 2404 within each opening 2422 and extends a full length of the corresponding opening. As used herein, the "length" of the at least one opening 2422 means a distance measured along a first radial axis RA1, as shown in FIG. 25. The surface area component 2408 is configured to increase the amount of surface within the opening 2422, and more generally, within the hollow wire 2402 for improved tissue in-growth as described in more detail below. While the roughness 2440 is shown with a specific pattern, this is by way of example and not limitation, and the roughness 2440 may assume other shapes, and/or patterns.

The surface area components 2408 may be positioned at select openings 2422 of the stent 2400 such as openings disposed on one or more crowns 2412, one or more struts 2410, or any combination thereof. In another embodiment, surface area components 2408 may be positioned at select openings 2422 disposed at the end portions of the stent 2400. Positioning of the surface area components 2408 at select openings 2422 of the stent 2400 may be utilized to encourage preferred tissue in-growth in select locations.

Figure 26A:
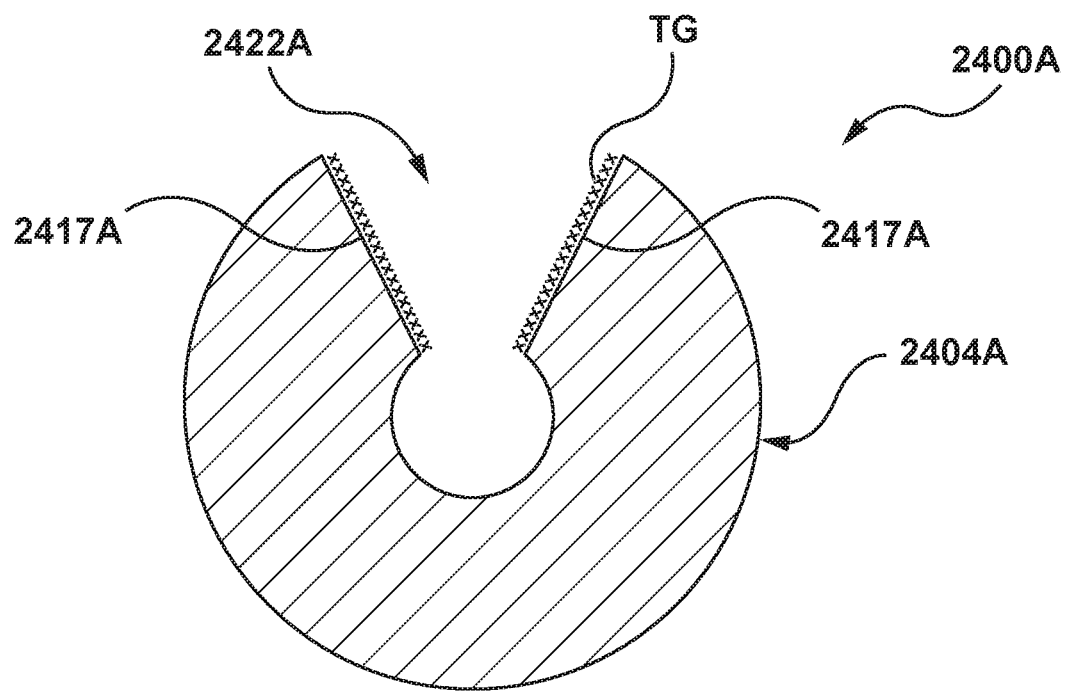
FIG. 26A is also a cross-sectional view of the hollow wire of FIG. 24, wherein the surface area component and the active agent have been omitted to illustrate a surface area within an opening without the surface area component.
Figure 26B:
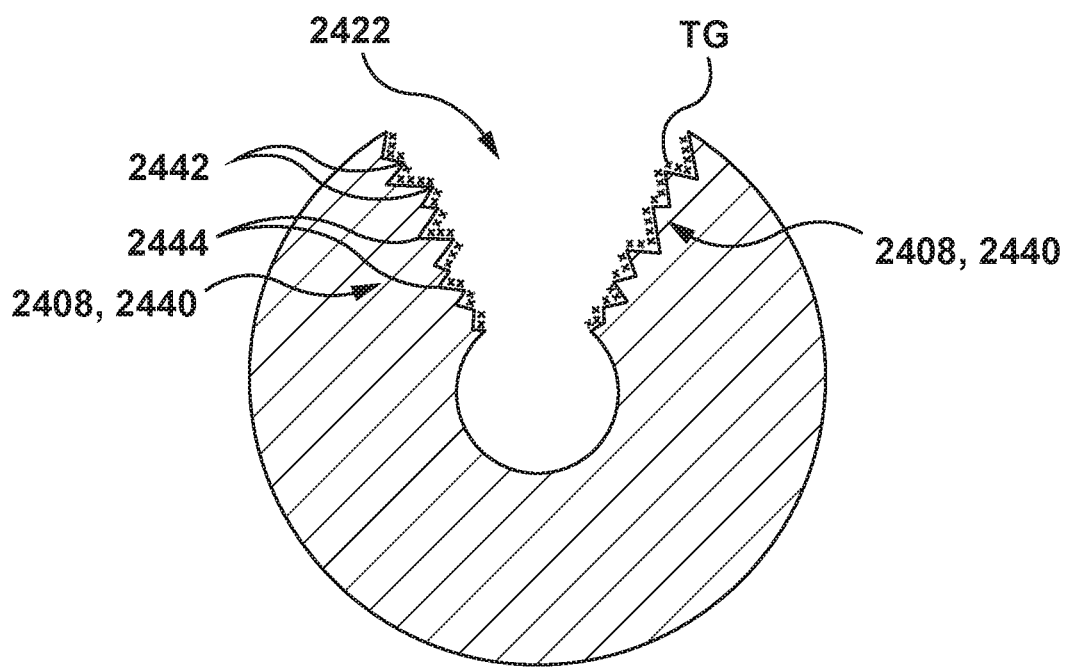
FIG. 26B is a cross-sectional view of the hollow wire of FIG. 24, wherein surface area component is shown to illustrate the increased amount of surface within the opening with the surface area component and to illustrate the tissue growth about the surface area component after the active agent has eluted in situ.

FIGS. 26A and 26B illustrate the stent 2400 without and with the roughness 2440 of the surface area component 2408, respectively, and are included herein to illustrate the increase in the amount of surface within the plurality of openings 2422 with the surface area component 2408. Referring to FIG. 26A, when the surface area component 2408 is not present, the surface area available for tissue in-growth within each opening 2422A is only the smooth radial surface 2417A of the outer member 2404A. Tissue TG may attach to the stent 2400A within each opening 2422A only along the smooth radial surface 2417A of the outer member 2404A. However, as shown in FIG. 26B, when the surface area component 2408, i.e., the roughness 2440 is included on the radial surface 2417 of the outer member 2404, the surface area available for tissue in-growth within each opening 2422 includes the roughened radial surface 2417 of the outer member 2404, including the surface areas of a plurality of peaks 2442 and a plurality of valleys 2444 formed in the radial surface 2417 of the outer member 2404. Due to the plurality of peaks 2442 and the plurality of valleys 2444, the roughened inner surface 2418 has a greater amount of surface or surface area than the smooth inner surface 2418A. Thus, the surface area component 2408 increases the amount of surface available for tissue TG in-growth within the plurality of openings 2422.

In the embodiment of FIG. 25, the biologically or pharmacologically active agent 190 previously described herein is deposited within the lumen 2406 of the hollow wire 2402. The ends 2426 of the hollow wire 2402 may be closed by crimping excess material of the hollow wire 2402 to close the lumen 2406. The ends 2426 may also be closed by not removing a core member during the method of manufacture thereof, from the ends 2426. In the embodiment of FIG. 25, with the active agent 2490 disposed within the lumen 2406, closing the ends 2426 prevents the active agent 2490 from prematurely releasing from the ends 2426. However, closing the ends 2426 is not required as the active agent 2490 may be dried, provided within a polymer matrix, enclosed within a liner (not shown in FIGS. 24 and 25), or otherwise protected from premature release from the ends 2426. Further, the ends 2426 may be welded, crimped or otherwise connected to other portions of the hollow wire 2402 such that the ends 2426 are not free ends.

When the stent 2400 is deployed within a vessel, the active agent 2490 elutes from the lumen 2406 of the stent 2400. Once the active agent 2490 has been eluted, cells originating from the vessel migrate into the plurality of openings 2422 and into the lumen 2406. The cells attach or couple to the surfaces within the plurality of openings 2422. More specifically, the cells couple to the radial surface 2417 of the outer member 2404, which includes the roughness 2440. Additionally, cells will migrate into the lumen 2406 and couple to the inner surface 2418 of the outer member 2404. Once attached thereto, the cells grow or colonize and form an extracellular matrix within the plurality of openings 2422 to couple the stent 2400 to the vessel. The increased amount of surface available within the plurality of openings 2422 of the hollow wire 2402 with the surface area component 2408 permits more cells to couple to the stent 2400, and thus more firmly anchors the stent 2400 to the vessel.

Figure 27:
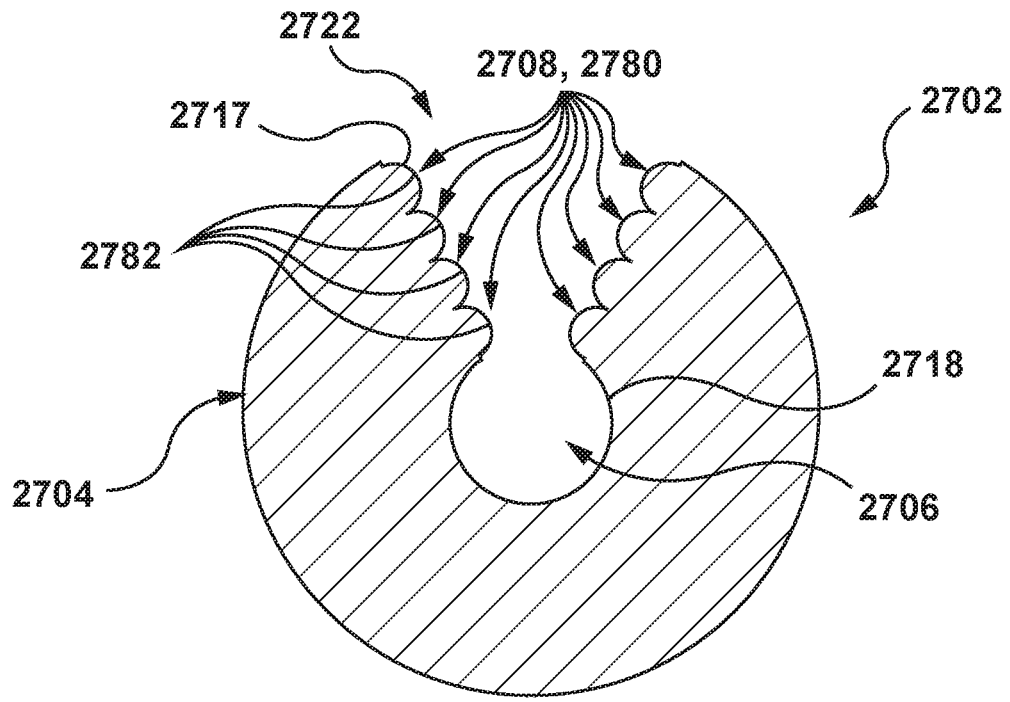
FIG. 27 is a cross-sectional view taken along line 27-27 of FIG. 24, wherein the stent includes a plurality of surface area components in accordance with another embodiment hereof, wherein each surface area component is a protrusion forming an increased amount of surface within an opening of the hollow wire.
Figure 28:
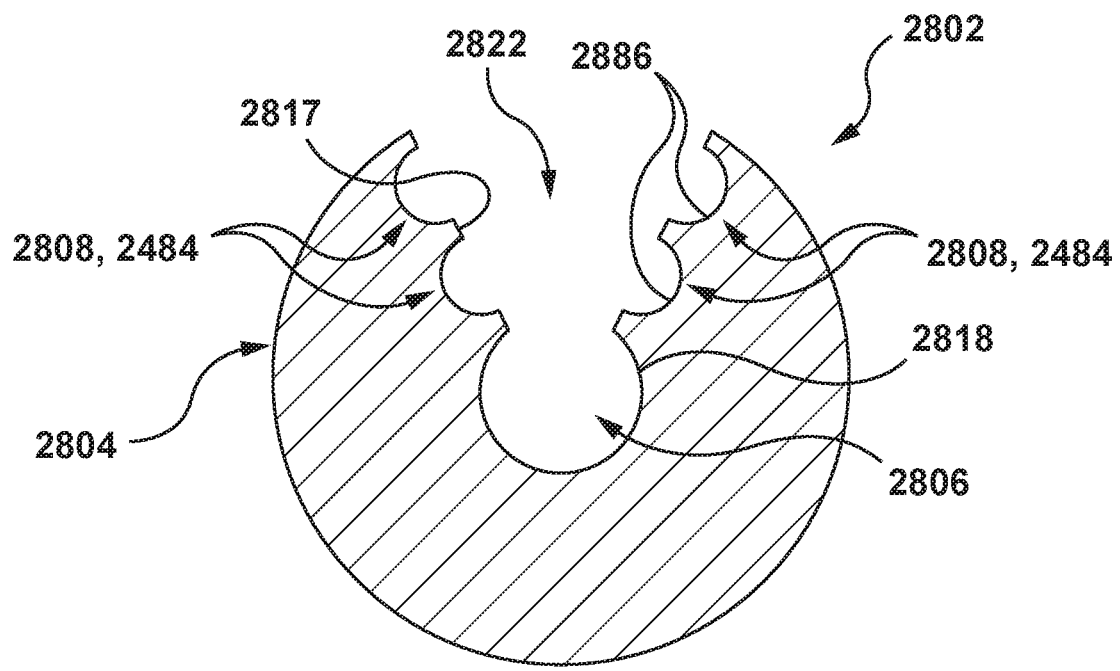
FIG. 28 is a cross-sectional view taken along line 28-28 of FIG. 24, wherein the stent includes a plurality of surface area components in accordance with another embodiment hereof, wherein each surface area component is a groove forming an increased surface area within an opening of the hollow wire.

While the surface area component 2408 is described as roughness in the embodiment of FIGS. 24-26B, the surface area component 2408 within the plurality of openings 2422 may be configured with other shapes. Accordingly, FIGS. 27 and 28 show various embodiments of the shapes and distribution of a plurality of surface area components within openings of a hollow wire. FIG. 27 shows a cross-sectional view of a hollow wire 2702 with an example of a plurality of surface area components 2708 within an opening 2722 according to another embodiment hereof. In the embodiment of FIG. 27, a radial surface 2717 of an outer member 2704 within the opening 2722 includes four (4) surface area components 2708. Each surface area component 2708 is a rounded protrusion 2780 extending circumferentially into the opening 2722 from the radial surface 2717. Each protrusion 2708 includes an outer surface 2782. Each protrusion 2780 is configured to increase the amount of surface within the opening 2722 of the hollow wire 2702 to improve the distribution of tissue in-growth to reduce micro-injuries resulting from biomechanical motion of the vessel as described in more detail below.

Each protrusion 2780 may be formed as a portion of the outer member 2704 through a process such as, but not limited to machining or chemical etching, or may alternatively be formed as a separate component and coupled to the radial surface 2717 of the outer member 2704 by methods such as, but not limited to adhesives, fusing, welding, or any other suitable method. In the embodiment of FIG. 27, each protrusion 2780 extends in a ring or annular pattern about the radial surface 2717 of the outer member 2704. However, this is by way of example and not limitation, and each protrusion 2717 may extend in other paths such as, but not limited to a helical pattern.

While shown with four (4) protrusions 2780 at specific locations, this is by way of example and not limitation, and a greater or lesser number of protrusion 2780 may be utilized with each protrusion 2780 positioned at any location along the radial surface 2717 of the outer member 2704 within the corresponding opening 2722. Even further, while each protrusion 2780 is shown with a specific shape and size, this too is by way of example and not limitation, and each protrusion 2780 may assume other shapes and sizes. Protrusions 2780 of different shapes may be utilized in any combination.

When a stent is formed from the hollow wire 2702 and deployed within a vessel, the stent elutes the active agent 190. Once the active agent 190 has been eluted, cells originating from the vessel migrate into the plurality of openings 2722. The cells attach or couple to the surfaces within the plurality of openings 2722. More specifically, the cells couple to the radial surface 2717 of the outer member 2704 and to the outer surface 2782 of each protrusion 2780. Cells will also migrate through the plurality of openings 2722 into the lumen 2706 and couple to the inner surface 2718 of the outer member 2704. Once attached thereto, the cells grow or colonize and form an extracellular matrix to couple the stent to the vessel as previously described.

FIG. 28 shows a cross-sectional view of a hollow wire 2802 with an example of a plurality of surface area components 2808 within a plurality of openings 2822 according to another embodiment hereof. In the embodiment of FIG. 28, a radial surface 2817 of an outer member 2804 within the opening 2822 includes two (2) surface area components 2808. Each surface area component 2808 is a channel or groove 2884 extending circumferentially away from the opening 2822 and into the outer member 2804 from the radial surface 2817 and includes an inner surface 2886. Each groove 2884 is configured to increase the amount of surface within the opening 2822 of the hollow wire 2802 to improve the distribution of tissue in-growth to reduce micro-injuries resulting from biomechanical motion of the vessel as described in more detail below.

Each groove 2884 may be formed into the radial surface 2817 of the outer member 2804 by methods such a chemical etching, machining, or any other suitable method. In the embodiment of FIG. 28, each groove 2884 extends in a ring or annular pattern about the radial surface 2817 of the outer member 2804. However, this is by way of example and not limitation, and each groove 2884 may extend in other paths such as, but not limited to a helical pattern.

While shown with two (2) grooves 2884 at specific locations, this is by way of example and not limitation, and a greater or lesser number of grooves 2884 may be utilized. Further, each groove 2884 may be positioned at any location along the radial surface 2817 of the outer member 2804 within the corresponding opening 2822. Even further, while each groove 2884 is shown with a specific size and shape, this too is by way of example and not limitation, and each groove 2884 may assume other sizes and shapes. It will be understood that grooves 2884 of different shapes may be utilized in any combination.

When a stent is formed from the hollow wire 2802 and deployed within a vessel, the stent elutes the active agent 190. Once the active agent 190 has been eluted, cells originating from the vessel migrate into the plurality of openings 2822. The cells attach or couple to the surfaces within the plurality of openings 2822. More specifically, the cells couple to the radial surface 2817 of the outer member 2804 and to the inner surface 2886 of each groove 2884. Additionally, cells migrate through the plurality of openings 2822 into the lumen 2806 and couple to the inner surface 2818 of the outer member 2804. Once attached thereto, the cells grow or colonize and form an extracellular matrix to couple the stent to the vessel as previously described.

Figure 29:
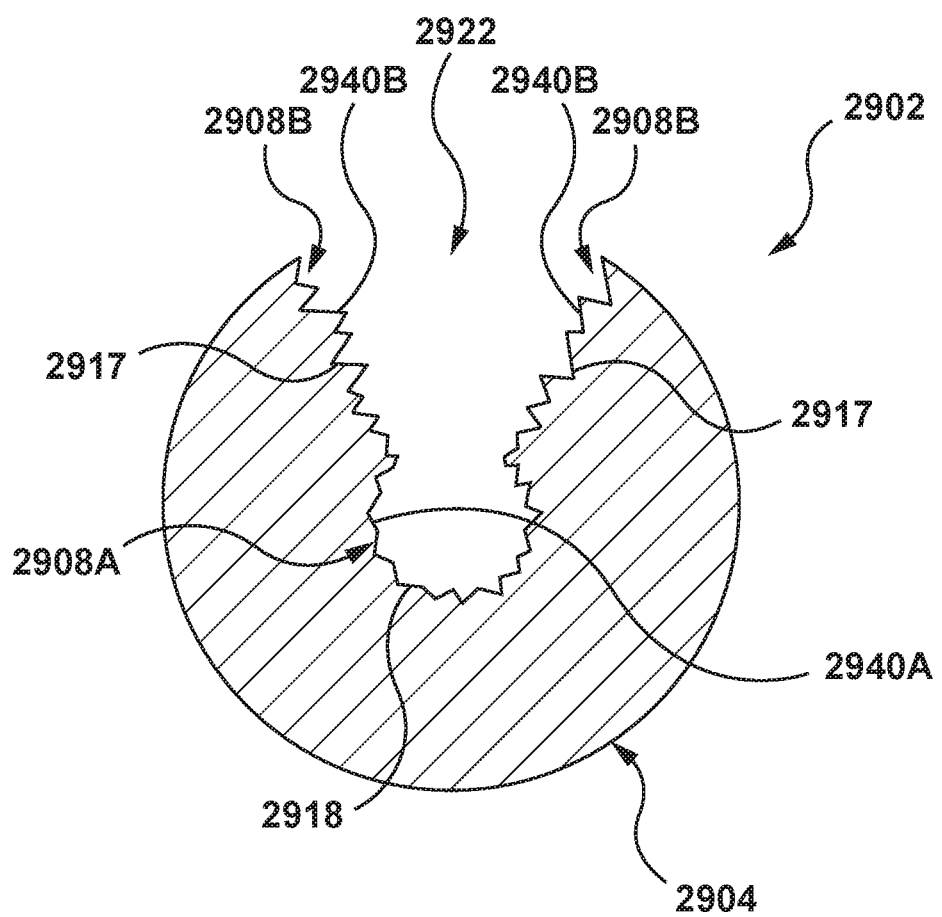
FIG. 29 is a cross-sectional view taken along line 29-29 of FIG. 24, wherein the stent includes two surface area components in accordance with another embodiment hereof, wherein a first surface area component is disposed on an inner surface of the outer member and a second surface area component is disposed on a radial surface defining the opening of the hollow wire.

Although surface area components have been presented and described herein as disposed on either an inner surface defining a lumen, or on a radial surface defining an opening, this is by way of example and not limitation. It will be understood by those skilled in the art that when a plurality of surface area components is present, each surface area components may be of a different shape and size, and that each surface area component may be placed at various locations along the radial surface of the outer member or the inner surface defining the lumen of the hollow wire. FIG. 29 illustrates a hollow wire 2902 in accordance with another embodiment hereof. The hollow wire 2902 includes a first surface area component 2908A disposed on an inner surface 2918 of an outer member 2904 and a second surface area component 2908B be disposed on a radial surface 2917 of defining an opening 2922. In the embodiment of FIG. 29, the first and second surface area components 2908A and 2908B are a roughness 2940A and 2940B. However, it will be understood by those skilled in the art that any embodiment of surface area component may be disposed at either location and in any combination.

While various embodiments according to the present invention have been described above, it should be understood that they have been presented by way of illustration and example only, and not limitation. Various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent comprising:
   a hollow wire formed into a stent pattern, wherein the hollow wire includes:
   a lumen extending longitudinally within the hollow wire to form the hollow wire;
   at least one opening disposed through the hollow wire to the lumen and defined by a radial surface;
   a biologically or pharmacologically active agent disposed in the lumen; and
   a surface area component disposed on an inner surface of the hollow wire defining the lumen,
   wherein the surface area component is discontinuous along a length of the hollow wire such that a plurality of segments are formed along the length of the hollow wire, and
   wherein the surface area component increases the amount of surface available for tissue in-growth within the hollow wire along the plurality of segments relative to an amount of surface available for tissue in-growth along the inner surface not having the surface area component disposed thereon.

2. The stent of claim 1, wherein the surface area component is a roughness on the inner surface of the hollow wire defining the lumen.

3. The stent of claim 1, wherein the surface area component is a channel on the inner surface of the hollow wire defining the lumen.

4. The stent of claim 1, wherein the surface area component is a ledge on the inner surface of the hollow wire defining the lumen.

5. The stent of claim 1, wherein the surface area component is a rounded protrusion on the inner surface of the hollow wire defining the lumen.

6. The stent of claim 1, wherein the surface area component is a groove on the inner surface of the hollow wire defining the lumen.

7. The stent of claim 1, wherein the hollow wire further includes:
   an outer member, and
   an intermediate member lining at least a portion of an inner surface of the outer member, the intermediate member having an outer surface and an inner surface, wherein the intermediate member is formed from a radiopaque material,
   wherein the lumen is defined by the inner surface of the intermediate member and extends longitudinally within the intermediate member, and wherein the at least one opening is disposed through the outer member and the intermediate member to the lumen.

8. The stent of claim 1, wherein a second surface area component is disposed on the radial surface defining the at least one opening.

9. The stent of claim 8, wherein the second surface area component is a roughness on the radial surface defining the at least one opening.

10. The stent of claim 8, wherein the second surface area component is a protrusion on the radial surface defining the at least one opening.

11. The stent of claim 8, wherein the second surface area component is a groove in the radial surface defining the at least one opening.

12. The stent of claim 1, wherein the plurality of segments are disposed at end portions of the stent.

13. A stent comprising:
a hollow wire formed into a stent pattern, wherein the hollow wire includes:
a lumen extending longitudinally within the hollow wire to form the hollow wire;
at least one opening disposed through the hollow wire to the lumen and defined by a radial surface, wherein a first diameter of the at least one opening at an outer surface of the hollow wire is greater than a second diameter of the lumen;
a first surface area component disposed on at least one radial surface of the at least one opening; and
a second surface area component disposed on an inner surface of the hollow wire defining the lumen,
wherein the second surface area component is discontinuous along a length of the hollow wire such that a plurality of segments are formed along the length of the hollow wire, and
wherein the second surface area component increases the amount of surface available for tissue in-growth within the hollow wire along the plurality of segments relative to an amount of surface available for tissue in-growth along the inner surface not having the second surface area component disposed thereon.

14. A stent comprising:
a hollow wire formed into a stent pattern, wherein the hollow wire includes:
a lumen extending longitudinally within the hollow wire to form the hollow wire;
a plurality of openings including at least a first opening and a second opening, each opening of the plurality of openings disposed through the hollow wire to the lumen and each opening of the plurality of openings defined by a radial surface; and
a surface area component disposed on the radial surface of the first opening of the plurality of openings,
wherein the surface area component is not disposed on the radial surface of the second opening of the plurality of openings, and
wherein the surface area component increases the amount of surface available for tissue in-growth along the radial surface of the first opening relative to an amount of surface available for tissue in-growth along the radial surface of the second opening.

15. The stent of claim 14, wherein the first opening is disposed at an end portion of the stent.

16. The stent of claim 14, wherein the surface area component is a roughness on the radial surface of the first opening.

17. The stent of claim 14, further comprising a biologically or pharmacologically active agent disposed in the lumen.

18. The stent of claim 14, wherein the surface area component is also disposed on an inner surface of the hollow wire defining the lumen.

* * * * *